United States Patent
Seoane Suarez et al.

(10) Patent No.: US 10,100,112 B2
(45) Date of Patent: Oct. 16, 2018

(54) THERAPEUTIC AGENTS FOR THE TREATMENT OF DISEASES ASSOCIATED WITH UNDESIRED CELL PROLIFERATION

(75) Inventors: Joan Seoane Suarez, Barcelona (ES); Silvia Penuelas Prieto, Barcelona (ES); José Baselga Torres, Barcelona (ES)

(73) Assignees: Fundacio Privada Institutcio Catalana de Recerca I Estudis Avancats (ICREA) (ES); Fundacio Privada Institut D'Investigatio Oncologica Vall De'Hebron (VHIO) (ES); Fundacio Privada Institut de Recerca Hospital Universitatri Vall Hebron (IR-HUVH) (ES)

( * ) Notice: Subject to any disclaimer, the term of this patent is extended or adjusted under 35 U.S.C. 154(b) by 0 days.

(21) Appl. No.: 13/138,804

(22) PCT Filed: Apr. 6, 2010

(86) PCT No.: PCT/EP2010/054499
§ 371 (c)(1),
(2), (4) Date: Jan. 18, 2012

(87) PCT Pub. No.: WO2010/115868
PCT Pub. Date: Oct. 14, 2010

(65) Prior Publication Data
US 2012/0114671 A1    May 10, 2012

(30) Foreign Application Priority Data
Apr. 3, 2009 (ES) .................................. 200900928

(51) Int. Cl.
| | |
|---|---|
| A61K 39/395 | (2006.01) |
| A61K 31/7115 | (2006.01) |
| A61K 31/7125 | (2006.01) |
| G01N 33/574 | (2006.01) |
| C07K 16/24 | (2006.01) |
| A61K 39/00 | (2006.01) |

(52) U.S. Cl.
CPC ........ *C07K 16/244* (2013.01); *A61K 31/7115* (2013.01); *A61K 31/7125* (2013.01); *A61K 2039/505* (2013.01); *C07K 2317/76* (2013.01); *G01N 33/574* (2013.01)

(58) Field of Classification Search
None
See application file for complete search history.

(56) References Cited

U.S. PATENT DOCUMENTS

| | | | | |
|---|---|---|---|---|
| 5,654,157 A | * | 8/1997 | Kim | ................................. 435/7.1 |
| 5,688,681 A | * | 11/1997 | Kim | ..................... C07K 16/244 |
| | | | | 435/335 |
| 2005/0147609 A1 | | 7/2005 | Filvaroff | |
| 2008/0113351 A1 | | 5/2008 | Naito et al. | |
| 2012/0308479 A1 | * | 12/2012 | Madden et al. | ............. 424/1.49 |

FOREIGN PATENT DOCUMENTS

| | | | |
|---|---|---|---|
| EP | 0 572 118 A1 | | 12/1993 |
| WO | WO 91/13985 | * | 9/1991 |
| WO | WO 93/23556 A1 | | 11/1993 |
| WO | WO 2005/030803 A1 | | 4/2005 |

OTHER PUBLICATIONS

Chuan Huang, Min Li, Changyi Chen & Qizhi Yao MD PhD (2008) Small interfering RNA therapy in cancer: mechanism, potential targets, and clinical applications, Expert Opinion on Therapeutic Targets, 12:5, 637-645.*
Pushparaj et al., J Dent Res 87(11):992-1003, 2008.*
Stiles, Neuron, 58:832-846, 2008.*
Huang et al., Chin J Oncol, 28(05): 331-333, 2006.*
Bauer, Sylvian, "Cytokine Control of Adult Neural Stem Cells, Chronic versus Acute Exposure," Annals of the New York Academy of Sciences, Feb. 1, 2009, 1153:48-56.
Colomiere et al., "Cross talk of signals between EGFR and IL-6R through JAK2/STAT3 mediate epithelial-mesenchymal transition in ovarian carcinomas," British Journal of Cancer, Jan. 1, 2009, 100(1):134-144.
Li et al. "Autocrine factors sustain glioblastoma stem cell self-renewal," Oncology Reports, Feb. 1, 2009, 21(2):419-424.
Peñuelas et al., "TGF-β Increases Glioma-Initiating Cell Self-Renewal through the Induction of LIF in Human Glioblastoma," Cancer Cell, Apr. 7, 2009, 15(4):315-327.
Ramaswamy et al., "Multiclass cancer diagnosis using tumor gene expression signatures," PNAS, Dec. 18, 2001, 98(26):15149-15154.
Ravandi et al., "The Role of Leukemia Inhibitory Factor in Cancer and Cancer Metastasis," Cancer Metastasis Biology and Treatment Growth Factors and their Receptors in Cancer Metastasis, Jan. 1, 2004, 2:1-25.
Zhu et al., "Combined microarray analysis uncovers self-renewal related signaling in mouse embryonic stem cells," Systems and Synthetic Biology, Dec. 1, 2007, 1(4):171-181.
Zvonic et al., "Cross-talk among gp130 Cytokines in Adipocytes," The Journal of Biological Chemistry, Oct. 1, 2005, 280(40):33856-33863.

(Continued)

*Primary Examiner* — Marianne P Allen
(74) *Attorney, Agent, or Firm* — Wilson Sonsini Goodrich & Rosati

(57) ABSTRACT

The present invention relates to inhibitors of the expression and/or activity of LIF for the treatment of cancer. Particularly, the present invention provides an in vitro method for designing a customized therapy for a patient suffering from cancer comprising (a) quantifying the expression levels of LIF in said patient, and (b) comparing said expression levels with control levels, wherein if the expression levels of LIF in said patient are greater than the control values, then an inhibitory agent of LIF is administered to said patient.

10 Claims, 12 Drawing Sheets

(56) References Cited

OTHER PUBLICATIONS

Alphonso et al., "Neutralizing monoclonal antibodies to human leukemia inhibitory factor (LIF)," Journal of Leukocyte Biology, Federation of American Societies for Experimental Biology, Jan. 1, 1991, Supp. 2, 49, 124, XP009175651.

Godard et al., "Generation of monoclonal antibodies against HILDA/LIF and their use in the quantitative assay of the cytokine," Cytokine, Jan. 1, 1993, 5(1):16-23, XP023271369.

Kellokumpu-Lehtinen et al., "Leukemia-inhibitory factor stimulates breast, kidney and prostate cancer cell proliferation by paracrine and autocrine pathways," Int. J. Cancer, Jan. 1, 1996, 66(4):515-519, XP009136742.

Lilja et al., "Expression of the IL-6 family cytokines in human brain tumors," International Journal of Oncology, Sep. 1, 2001, 19(3):495-499.

Lo et al., "Constitutively Activated STAT3 Frequently Coexpresses with Epidermal Growth Factor Receptor in High-Grade Gliomas and Targeting STAT3 Sensitized Them to Iressa and Alkylators," Clinical Cancer Research, Oct. 1, 2008, 14(19):6042-6054.

Bao et al., "Glioma stem cells promote radioresistance by preferential activation of the DNA damage response," Nature, Dec. 2006, 444:756-760.

Halfter et al., "Inhibition of Growth and Induction of Differentiation of Glioma Cell Lines by Oncostatin M (OSM)," Growth Factor, 1998, 15:135-147.

Laks et al., "Neurosphere Formation Is an Independent Predictor of Clinical Outcome in Malignant Glioma," Stem Cells, 2009, 27:980-987.

Lee et al., "Tumor stem cells derived from glioblastomas cultured in bFGF and EGF more closely mirror the phenotype and genotype of primary tumors than do serum-cultured cell lines," Cancer Cell, May 2006, 9:391-403.

Singh et al., "Identification of human brain tumour initiating cells," Nature, Nov. 18, 2004, 432:396-401.

Stupp et al., "Targeting brain-tumor stem cells," Nature Biotechnology, Feb. 2007, 25(2):193-194.

Quaglino et al., "Mouse mammary tumors display Stat3 activation dependent on leukemia inhibitory factor signaling," Breast Cancer Research, 2007, 9(5):R69, 1-12.

Halfter et al., "Growth inhibition of newly established human glioma cell lines by leukemia inhibitory factor," Journal of Neuro-Oncology, 1998, 39:1-18.

Rahaman et al., "Inhibition of constitutively active Stat3 suppresses proliferation and induces apoptosis in glioblastoma multiforme cells," Oncogene, 2002, 21:8404-8413.

Zaheer et al., "Expression of mRNAs of Multiple Growth Factors and Receptors by Astrocytes and Glioma Cells: Detection with Reverse Transcription—Polymerase Chain Reaction," Cellular and Molecular Neurobiology, 1995, 15(2):221-237.

\* cited by examiner

THERAPEUTIC AGENTS FOR THE TREATMENT OF DISEASES ASSOCIATED WITH UNDESIRED CELL PROLIFERATION

CROSS-REFERENCE TO RELATED APPLICATIONS

This application is a National Stage application of PCT/EP2010/054499, filed Apr. 6, 2010, which claims priority from ES P200900928, filed Apr. 3, 2009.

DESCRIPTION OF THE INVENTION

Field of the Invention

The present invention generally relates to inhibitors of the expression and/or activity of an IL-6 type cytokine for the treatment of diseases associated with unwanted cell proliferation, more particularly, for cancer and tumor stem cells. Likewise, a method for the diagnosis of said diseases and for prognosis of average life expectancy of patients is also described.

State of the Art

A sub-population of tumor cells with stem cell-like properties has recently been discovered in cancer. It is considered that this cell population, referred to as cancer stem cells, are responsible for the onset, propagation and recurrence of the tumors, indicating that the most effective therapies come from therapies directed at the compartmentalization of tumor stem cells. Little is known with respect to the molecular characteristics and regulating mechanisms controlling the biology of tumor stem cells. One of the tumors in which tumor stem cells play a significant role is glioma, so-called glioma stem cells or glioma initiating cells (GICs).

GICs are characterized by their high oncogenic potential, their capacity for self-renewal and their capacity of differentiating into multiple cell lines. The number of stem cell-like cells in a tumor is regulated by its capacity of self-regeneration. Gies and, generally, cancer stem cells experience symmetric and asymmetric divisions by means of which a stem cell generates two identical copies thereof or a copy of the stem cell and a more differentiated cell (asymmetric division). The capacity of self-regeneration of the cancer stem cell is regulated by the balance between the symmetric and asymmetric divisions and the deregulation of the mechanisms controlling said self-renewal is most likely involved in the onset of the tumor.

Glioma is the most common primary tumor of the brain and can be classified in four clinical grades depending on its histology and prognosis. Grade IV gliomas (glioblastoma multiforme) are highly aggressive and resistant to both radiotherapy and chemotherapy. Despite progress in understanding the molecular mechanisms involved in the genesis and progression of glioma, the prognosis and the treatment of this type of tumor continues to be ineffective. The treatment of choice for glioma is surgical intervention. Nevertheless, surgical treatment is usually accompanied by a pharmacological adjuvant treatment or by means of radiotherapy. The drugs of choice for the treatment of glioma include the combination referred to as PCV which comprises procarbazine, CCNU (lomustine) and vincristine, temozolomide in combination with radiotherapy.

It is considered that GICs are responsible for the onset, propagation and recurrence of tumors, indicating that the most effective therapies will come from therapies directed at compartmentalizing glioma stem cells. A tumor will not be eradicated if GICs are not eliminated.

Therefore, it is necessary to have alternative treatments which prevent the drawbacks of treatments known in the state of the art and which can efficiently eliminate GICs.

SUMMARY OF THE INVENTION

In a first aspect, the invention relates to an inhibitory agent of the expression and/or the activity of an IL-6 type cytokine for the treatment of diseases associated with unwanted cell proliferation.

In another aspect, the invention relates to a pharmaceutical composition comprising a therapeutically effective amount of an inhibitory agent according to the invention and a pharmaceutically acceptable carrier for the treatment of diseases associated with unwanted cell proliferation.

In another aspect, the invention relates to an in vitro method for the identification of compounds capable of blocking/inhibiting the cell proliferation of tumor cells induced by an IL-6 type cytokine or a functionally equivalent variant thereof comprising the steps of:
(i) contacting a cell expressing the receptor for an IL-6 type cytokine with an IL-6 type cytokine and a candidate compound, and
(ii) identifying those compounds blocking the cell proliferation of said cell.

In another aspect, the invention relates to an in vitro method for the diagnosis of diseases associated with unwanted cell proliferation in a subject or for determining the predisposition of a subject to suffer said disease associated with unwanted cell proliferation, or for determining the stage or severity of said disease associated with unwanted cell proliferation in a subject, or for monitoring the effect of the therapy administered to a subject with said disease associated with unwanted cell proliferation, which comprises quantifying the expression levels of the gene encoding an IL-6 type cytokine or of the protein encoded by said gene or functionally equivalent variant of said protein in a biological sample from said subject, in which an increase of the expression of the gene encoding an IL-6 type cytokine or of the protein encoded by said gene or functionally equivalent variant of said protein, with respect to the expression of the gene encoding an IL-6 type cytokine or of the protein encoded by said gene or functionally equivalent variant of said protein in a control sample, is indicative of a disease associated with unwanted cell proliferation, or of greater predisposition of said subject to suffer from a disease associated with unwanted cell proliferation or of the non-response to the therapy administered to said subject. In another aspect, the invention relates to the use of a kit comprising reagents for the quantification of the expression levels of the gene encoding an IL-6 type cytokine or of the protein encoded by said gene or functionally equivalent variant of said protein for the diagnosis of cancer in a subject or for determining the predisposition of a subject to suffer said cancer, or for determining the stage or severity of said cancer in a subject, or for predicting the probability of survival and/or of the average expected life time of a subject suffering from said cancer, or for monitoring the effect of the therapy administered to a subject with said cancer, in which if the reagents detect an increase in the expression of said gene or said protein or functionally equivalent variant thereof with respect to a control sample, then said subject can suffer from a disease associated with unwanted cell proliferation, or presents a greater predisposition to suffer said disease associated with unwanted cell proliferation, or

DRAWINGS

DETAILED DESCRIPTION OF THE INVENTION

Therapeutic Methods of the Invention

Figure 1:
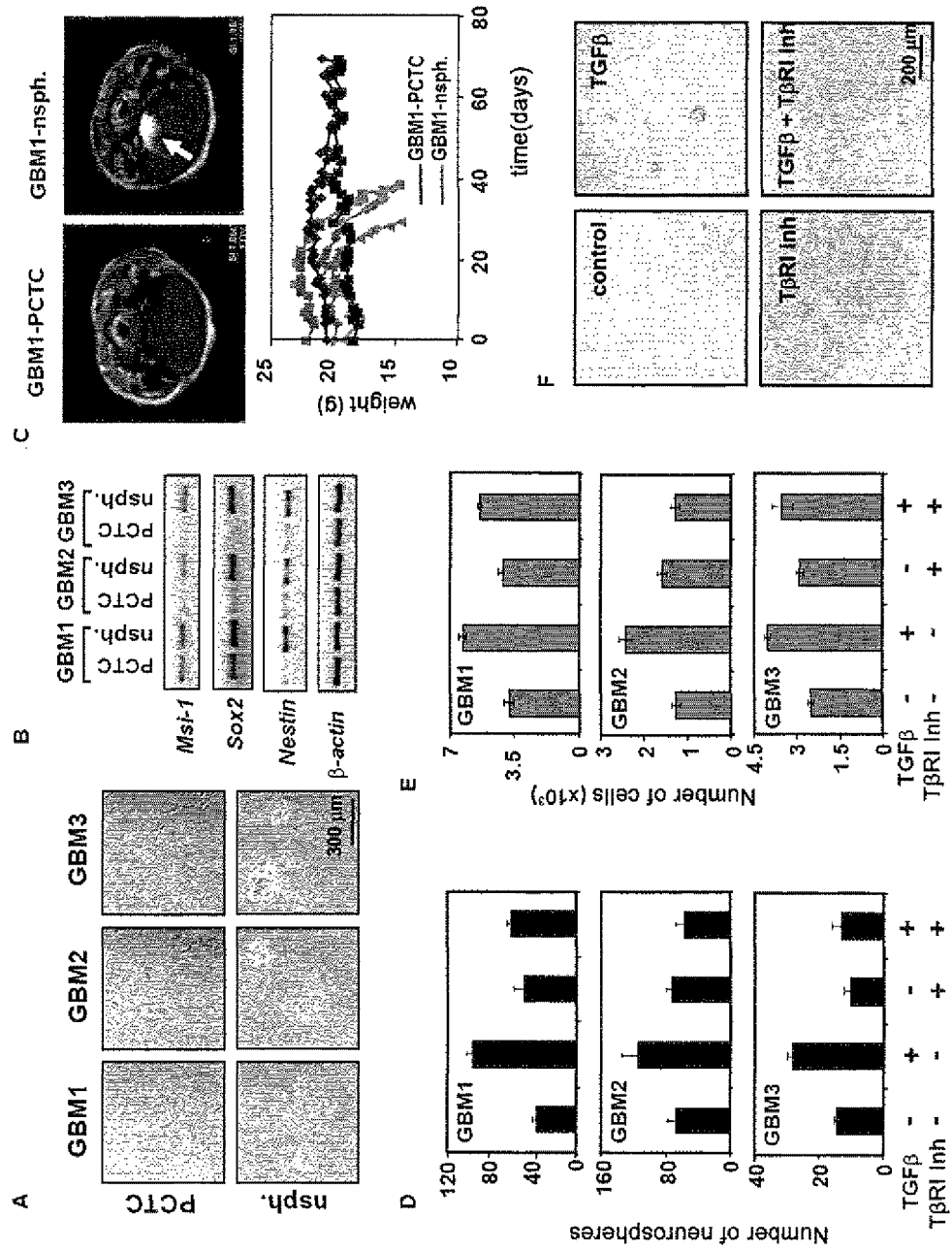
FIG. 1. Effect of TGFβ on the self-renewal of GIC derived from patients. (A) Representative images of PCTCs and neurospheres of GBM generated from samples of 3 different patients with GBM (GBM1, GBM2, GBM3). (B) Musashi-1 (Msi-1), Sox2, Nestin and β-actin were determined by means of RT-PCR analysis of PCTCs and neurospheres of 3 samples of human GBM. (C) 100,000 neurosphere (nsph.) or PCTC cells obtained from samples of GBM1, GBM2 and GBM3 tumors were intracranially inoculated in three Balbc nu/nu mice in each case. Magnetic resonance imaging (MRI) studies were performed on days 30-40 in each mouse. The images represent an example of mice inoculated with neurosphere or PCTC cells obtained from GBM1. The mice were weighed twice a week. The graph represents mice inoculated with cells derived from GBM1. (D and E) Neurosphere cells of the indicated GBMs were incubated in the absence of growth factors with 100 pM TGFβ1 and/or 2 µM TβRI inhibitor for 7 days and the number of newly formed neurospheres (D) and the total number of cells (B) were determined. (F) Representative images of GBM1 neurospheres treated as indicated in D and E.

The authors of the present invention have found that, surprisingly, an IL-6 type cytokine, more specifically LIF, is involved in the activation of the JAK-STAT cascade mediated by TGFβ, thus inducing the cell proliferation process and the increase of tumor stem cells (cancer stem cells). Based on this fact, the inventors have opened a new therapeutic window for the treatment of diseases associated with unwanted cell proliferation, such as cancer for example, and especially for the treatment of cancer caused by high activity of the JAK-STAT signaling pathway, said therapy being based on the use of inhibitors of IL-6 type cytokines. The identification of LIF as an element down-stream from TGFβ in the activation of JAK-STAT additionally allows a more efficient inhibition of said JAK-STAT cascade because it prevents its activation not only when it is activated by TGFβ, but also by any other stimulus, such as interleukins, erythropoietin, growth hormone, prolactin and the like.

Therefore, in one aspect, the invention relates to an inhibitory agent of the expression and/or the activity of an IL-6 type cytokine for the treatment of diseases associated with unwanted cell proliferation.

Without wishing to be bound by any theory, it is thought that the effect of LIF and of its inhibitors on the proliferation of tumors lies in the capacity of LIF to promote the proliferation of tumor stem cells. The treatment with LIF inhibitors would therefore be especially indicated in those tumors in which there is a high expression of IL-6 type cytokine, and more specifically in LIF. It would also be of interest for the treatment of tumors resistant to chemotherapy given the known capacity of tumor stem cells of being resistant to chemotherapy. Finally, given that tumor stem cells seem to be responsible for the relapses, the use of LIF inhibitors for the treatment of diseases associated with unwanted cell proliferation would be particularly suitable to prevent the occurrence of relapses.

Therefore, in a first aspect the invention relates to an inhibitory agent of the expression and/or the activity of an IL-6 type cytokine for the treatment of diseases associated with unwanted cell proliferation.

In another aspect, the invention relates to a method for the treatment of diseases associated with unwanted cell proliferation comprising the administration of an inhibitory agent of the expression and/or the activity of an IL-6 type cytokine.

In another aspect, the invention relates to an inhibitory agent of the expression and/or the activity of an IL-6 type cytokine for the production of a pharmaceutical composition for the treatment of diseases associated with unwanted cell proliferation.

In the context of the present invention, "IL-6 type cytokine" is understood as a cytokine member of the IL-6 family, comprising IL-6, IL-11, leukemia inhibitory factor (LIF), oncostatin M (OSM), cardiotrophin-1 (CT-1), ciliary neurotrophic factor (CNTF) and cardiotrophin-like cytokine (CLC) and activating the Jak-STAT signaling pathway. These cytokines share the same receptor complex in which the subunit of the glycoprotein-130 (130) receptor is a common constituent.

Therefore, in a particular embodiment of the invention, the IL-6 type cytokine is selected from LIF, IL-6, IL-11, oncostatin M, cardiotrophin-1, CNTF and CLC. In another yet more particular embodiment, the IL-6 type cytokines is LIF.

In the context of the present invention "inhibitory agent" is understood as any substance or compound that is capable of preventing or blocking the transcription and the translation of a gene encoding an IL-6 type cytokine (i.e., preventing or blocking the expression of said gene), or that is capable of preventing the protein encoded by said gene from performing its function (activity), i.e., preventing an IL-6 type cytokine from being able to induce the activation of the JAK-STAT signaling pathway. Assays for determining if a compound is an inhibitory agent of an IL-6 type cytokine are well known in the state of the art. For example, Mezt S. et al., (J. Biol. Chem, 2007, vol. 282:1238-1248) describe an assay based on the capacity of the inhibitor to block the expression of a reporter gene which is under the control of a promoter sensitive to an IL-6 cytokine. In the specific case of LIF, assays for the identification of inhibitory agents include the inhibition of M1 murine myeloid leukemia cell differentiation in the absence of LIF (WO2005/30803), inhibition of the stimulation of the release of calcium from Jurkatt cells (U.S. Pat. No. 5,980,894), measurement of STAT-3 phosphorylation by IL-6 type cytokine (see Example 2, section 2.4 of the examples of the present specification), etc.

By way of illustration, inhibitory agents of the expression of LIF suitable for their use in the present invention are, for example, antisense oligonucleotides, interference RNAs (siRNAs), catalytic RNAs or specific ribozymes, RNA with decoy activity, i.e., with capacity to bind specifically to a factor (generally proteinaceous) important for the expression of the gene, etc. Likewise, inhibitory agents capable of preventing the protein encoded by said gene encoding an IL-6 type cytokine from performing its function are, for example, inhibitory peptides of the protein, antibodies directed specifically against epitopes of the protein essential for carrying out its function, or against IL-6 type cytokine receptors, etc.

Therefore, in a particular embodiment of the invention, the inhibitory agent is selected from the group consisting of siRNAs, antisense oligonucleotides, specific ribozymes, antibodies, polypeptides and inhibitors of the IL-6 type cytokine receptor.

siRNA

Small interfering RNAs, or siRNAs, are agents which are capable of inhibiting the expression of a target gene by means of RNA interference. An siRNA can be chemically synthesized, can be obtained by means of in vitro transcription or can be synthesized in vivo in the target cell. siRNA typically consists of double-stranded RNA of between 15 and 40 nucleotides in length and it can contain a 3' and/or 5' overhang region of 1 to 6 nucleotides. The length of the overhang region is independent of the total length of the siRNA molecule. siRNAs act by means of degradation or post-transcriptional silencing of the target messenger.

siRNAs can be called shRNA (short hairpin RNA) characterized in that the antiparallel strands forming the siRNA are connected by a loop or hairpin region. These siRNAs are compounds of a short antisense sequence (from 19 to 25 nucleotides), followed by a loop of between 5 and 9 nucleotides which is followed by the sense strand. shRNAs can be encoded by plasmids or viruses, particularly retroviruses and, more particularly, retroviruses and can be under the control of promoters such as the U6 promoter of the RNA polymerase III.

The siRNAs of the invention are substantially homologous to the mRNA of the gene encoding an IL-6 type cytokine or to the genomic sequence encoding said protein. "Substantially homologous" is understood as having a sequence which is sufficiently complementary or similar to the target mRNA such that the siRNA is capable of causing the degradation of the latter by RNA interference. The siRNAs suitable for causing said interference include siRNA formed by RNA, as well as siRNA containing different chemical modifications such as:
 siRNA in which the bonds between the nucleotides are different from those found naturally, such as phosphorothioate bonds.
 conjugates of the RNA strand with a functional reagent, such as a fluorophore.
 Modifications of the ends of the RNA strands, particularly the 3' end by means of the modification with different functional groups of the hydroxyl at position 2'.
 Nucleotides with modified sugars such as O-alkylated residues at position 2' such as 2'-O-methylribose p 2'-O-fluororibose.
 Nucleotides with modified bases such as halogenated bases (for example 5-bromouracil and 5-iodouracil), alkylated bases (for example 7-methylguanosine).

The siRNA and shRNA of the invention can be obtained using a series of techniques known by the person skilled in the art. For example, the siRNA can be chemically synthesized from ribonucleosides protected with phosphoramidites in a conventional DNA/RNA synthesizer. Alternatively, the siRNA can be produced in a recombinant manner from plasmid and viral vectors in which case the region encoding the strand or strands forming the siRNA is under the operative control of RNA polymerase III promoters. In the cells, the Dicer RNase processes the shRNA into functional siRNA.

The region of the nucleotide sequence which is taken as a basis for designing siRNA is not limiting and can contain a region of the encoding sequence (between the start codon and the end codon), or it can alternatively contain sequences of the 5' or 3' non-translated region, preferably between 25 and 50 nucleotides in length and in any position at position 3' with respect to the start codon. One way of designing an siRNA involves the identification of the $AA(N_{19})TT$ motifs in which N can be any nucleotide in the sequence encoding an IL-6 type cytokine and selecting those which have a high G/C content. If said motif is not found, it is possible to identify the $NA(N_{21})$ motif in which N can be any nucleotide.

Antisense Oligonucleotides

An additional aspect of the invention relates to the use of isolated "antisense" nucleic acids to inhibit expression, for example inhibiting the transcription and/or translation of a nucleic acid encoding type IL-6 cytokine, the activity of which is to be inhibited. Antisense nucleic acids can bind to the potential drug target by means of conventional base complementarity, or, for example, in the case of binding to double-stranded DNA, through specific interactions in the major groove of the double helix. These methods generally relate to the range of techniques generally used in the art, and include any method which is based on the specific binding to oligonucleotide sequences.

An antisense construct of the present invention can be delivered, for example, as an expression plasmid which, when transcribed in the cell, produces RNA complementary to at least a single part of the cell mRNA encoding an IL-6 type cytokine. Alternatively, the antisense construct is an oligonucleotide probe, which is generated ex vivo and which, when introduced in the cell, produces inhibition of the expression by hybridizing with the mRNA and/or genomic sequences of a target nucleic acid. Such oligonucleotide probes are preferably modified oligonucleotides which are resistant to endogenous nucleases, for example, exonucleases and/or endonucleases, and which are therefore stable in vivo. Exemplary nucleic acid molecules for their use as antisense oligonucleotides are phosphoramidate, phosphothionate and methylphosphonate DNA analogs (also see U.S. Pat. Nos. 5,176,996; 5,264,564; and 5,256,775). General approaches for constructing oligomers useful in antisense therapy have additionally been reviewed, for example, in Van der Krol et al., BioTechniques 6: 958-976, 1988; and Stein et al., Cancer Res 48: 2659-2668, 1988.

With respect to antisense DNA, the regions of oligodeoxyribonucleotides derived from the translation initiation site, for example, between −10 and +10 of the target gene, are preferred. Antisense approaches involve the design of oligonucleotides (either DNA or RNA) which are complementary to the mRNA encoding the target polypeptide. Antisense oligonucleotides will bind to the mRNA transcripts and prevent translation. Absolute complementarity is not required, though it is preferred. In the case of double-stranded antisense nucleic acids, a single strand of the double-stranded DNAs can thus be assayed, or the formation of triple-stranded DNAs can be assayed. The capacity of hybridizing will depend both on the degree of complementarity and on the length of the antisense nucleic acid. Generally, the longer the nucleic acid hybridizing, the more RNA pairing errors it may contain and it still forms a stable duplex (or triplex, as the case may be). The person skilled in the art can determine a tolerable degree of pairing errors by means of the use of standard processes for determining the melting point of the hybridized complex.

Oligonucleotides which are complementary to the 5' end of the mRNA, for example the non-translated 5' sequence up to and including the AUG start codon, must function as effectively as possible in order to inhibit translation. However, it has recently been shown that the sequences complementary to the non-translated 3' sequences of mRNA are also effective for inhibiting the translation of mRNAs (Wagner, Nature 372: 333, 1994). Therefore, oligonucleotides complementary to either the non-translated, non-encoding 5' or 3' regions of a gene could be used in an antisense approach to inhibit the translation of that mRNA. Oligonucleotides complementary to the non-translated 5' region of the mRNA should include the complement of the AUG start codon. Oligonucleotides complementary to the encoding regions of mRNA are less effective inhibitors of translation but they could also be used according to the invention. If designed to hybridize with the 5', 3' or encoding region of mRNA, antisense nucleic acids should have at least six nucleotides in length, and preferably have less than about 100 and more preferably less than about 50, 25, 17 or 10 nucleotides in length.

It is preferred that in vitro studies are conducted first to quantify the capacity of the antisense oligonucleotides of inhibiting gene expression. It is preferred that these studies use controls distinguishing between antisense gene inhibition and non-specific biological effects of the oligonucleotides. It is also preferred that these studies compare the levels of RNA or target protein with that of an internal RNA or protein control. The results obtained using antisense oligonucleotides can be compared with that obtained using a control oligonucleotide. It is preferred that the control oligonucleotide is of the same length as the oligonucleotide to be assayed and that the oligonucleotide sequence differs from the antisense sequence no more than what is necessary to prevent specific hybridization to the target sequence.

Antisense oligonucleotides can be of DNA or RNA or chimeric mixtures or modified derivatives or versions thereof, single-stranded or double-stranded. Oligonucleotide can be modified in the base group, the sugar group, or the phosphate backbone, for example to improve the stability of the molecule, hybridization etc. The oligonucleotide can include other bound groups such as peptides (for example, to direct them towards host cell receptors), or agents to make transport through the cell membrane easier (see, for example, Letsinger et al., Proc. Natl. Acad. Sci. U.S.A. 86: 6553-6556, 1989; Lemaitre et al., Proc. Natl. Acad. Sci. 84: 648-652, 1987; Publication of PCT No. WO88/09810) or the blood-brain barrier (see, for example, publication of PCT No. WO89/10134), hybridization triggered cleaving agents (see, for example, Krol et al., BioTechniques 6: 958-976, 1988), intercalating agents (see, for example, Zon, Pharm. Res. 5: 539-549, 1988). For this purpose, the oligonucleotide can be conjugated to another molecule, for example, a peptide, a hybridization triggered cross-linking agent, a carrier agent, a hybridization triggered cleaving agent, etc.

Antisense oligonucleotides can comprise at least one modified base group which is selected from the group including but not limited to 5-fluorouracil, 5-bromouracil, 5-chlorouracil, 5-iodouracil, hypoxanthine, xanthine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide can also comprise at least one modified sugar group selected from the group including but not limited to arabinose, 2-fluoroarabinose, xylulose, and hexose. The antisense oligonucleotide can also contain a backbone similar to neutral peptide. Such molecules are referred to as peptide nucleic acid (PNA) oligomers and are described, for example, in Perry-O'Keefe at al., Proc. Natl. Acad. Sci. U.S.A. 93: 14670, 1996, and in Eglom at al., Nature 365: 566, 1993. An advantage of PNA oligomers is their capacity to bind to complementary DNA in a manner essentially independent of the ion force of the medium due to the neutral backbone of DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphorodiamidate, a methylphosphonate, an alkyl phosphotriester, and a formacetal or analog thereof.

In yet another embodiment, the antisense oligonucleotide is an alpha-anomeric oligonucleotide. An alpha-anomeric oligonucleotide forms specific double-stranded hybrids with complementary RNA in which, in contrast with the typical antiparallel orientation, the strands are parallel to one another (Gautier et al., Nucl. Acids Res. 15: 6625-6641, 1987). The oligonucleotide is a 2'-O-methylribonucleotide (Inoue et al., Nucl. Acids Res. 15: 6131-6148, 1987) or an RNA-DNA chimeric analog (Inoue et al., FEBS Lett. 215: 327-330, 1987).

While antisense oligonucleotides complementary to the encoding region of the target mRNA sequence can be used, those complementary to the non-translated transcribed region can also be used.

In some cases, it may be difficult to reach intracellular concentrations of the antisense sufficient for suppressing the translation of the endogenous mRNAs. Therefore, a preferred approach uses a recombinant DNA construct in which the antisense oligonucleotide is placed under the control of a strong pol III or pol II promoter. The use of such construct for transfecting target cells will result in the transcription of sufficient amounts of single-stranded RNAs which will form complementary base pairs with the potential target endogenous transcripts of drugs and will therefore prevent translation. For example, a vector can be introduced such that it is captured by a cell and directs the transcription of an antisense RNA. Such vector can remain episomal or be integrated in the chromosome, while it can be transcribed to produce the desired antisense RNA. Such vectors can be constructed by means of methods of recombinant DNA technology standard in the art. The vectors can be viral plasmids, or other plasmids known in the art used for replication and expression in mammal cells. The expression of the sequences encoding the antisense RNA can be by means of any promoter known in the art which acts on mammal cells, preferably human cells. Such promoters can be inducible or constitutive. Such promoters include but are not limited to: promoter of the SV40 early region (Bernoist and Chambon, Nature 290: 304-310, 1981), the promoter contained at 3' long repetition terminal of the Rous sarcoma virus (Yamamoto et al., Cell 22: 787-797, 1980), the herpes thymidine kinase promoter (Wagner et al., Proc. Natl. Acad. Sci. U.S.A. 78: 1441-1445, 1981), the metallothionein gene regulatory sequences (Brinster et al., Nature 296: 39-42, 1982), etc. Any type of plasmid, cosmid, YAC or viral vector can be used to prepare the recombinant DNA construct, which can be introduced directly in the site of the tissue.

The expression of the target gene can alternatively be expressed by directing complementary deoxyribonucleotide sequences to the regulatory region of the gene (i.e., the promoter and/or enhancers) to form triple helix structures preventing the transcription of the gene in the target cells in the body (see, generally, Helene, Anticancer Drug Des. 6(6): 569-84, 1991; Helene et al., Ann. N. E. Acad. Sci., 660: 27-36, 1992; and Maher, Bioassays 14(12): 807-15, 1992).

The nucleic acid molecules which will be used in the formation of triple helices for the inhibition of transcription are preferably single-stranded and formed by deoxyribonucleotides. The base composition of these oligonucleotides must enhance the formation of triple helices through the Hoogsteen base pairing rules, which generally require the presence of fairly large sections of purines or pyrimidines in a strand of a duplex. The nucleotide sequences can be based on pyrimidines, which will result in TAT and CGC triplets through the three associated strands of the resulting triple helix. The molecules rich in pyrimidine provide base complementarity to a region rich in single-stranded purines of the duplex in an orientation parallel to said strand. Furthermore, nucleic acid molecules which are rich in purines, for example, which contain a section of G residues, can be chosen. These molecules will form a triple helix with a double-stranded DNA which is rich in GC pairs, in which most of the purine residues are located in a single strand of the target duplex, resulting in CGC triplets through the three strands in the triplet.

The potential target sequences which can be selected for the formation of triple helices can alternatively be increased, creating a nucleic acid molecule called "hairpin-shaped". The hairpin-shaped molecules are synthesized in an alternating 5'-3',3'-5' form, such that they form a first base pair with a strand of a duplex and then with the other one, eliminating the need for the presence of a rather large section of purines or pyrimidines in a strand of a duplex.

In some embodiments, the antisense oligonucleotides are antisense morpholines. Morpholines are synthetic molecules that are the product of a redesign of natural nucleic acid structure. Typically 25 bases in length, they bind to complementary RNA sequences by means of standard nucleic acid base pairing. Structurally speaking, the difference between morpholines and DNA is that even though morpholines have standard nucleic acid bases, these bases bind to morpholine rings instead of deoxyribose rings, and they bind by means of phosphorodiamidate groups instead of phosphates. Switching anionic phosphates with neutral phosphorodiamidate groups eliminates ionization in the normal physiological pH range, such that morpholines in cells or organisms are uncharged molecules. Morpholines are not chimeric oligos; the entire backbone of a morpholine is made of these modified subunits. Morpholines are more commonly used as single-stranded oligos, although heteroduplexes of a morpholine strand and a complementary DNA strand can be used in combination with cationic reagents with cytosolic distribution.

Unlike many antisense structural types (for example phosphorothioates), morpholines do not degrade their target RNA molecules. In contrast, morpholines act by means of "steric hindrance", binding to a target sequence in an RNA and simply being placed in the path of molecules which could otherwise interact with the RNA. Morpholine oligos are commonly used to investigate the role of a specific mRNA transcript in an embryo, such as eggs, or embryos of zebrafish, African clawed frogs (Xenopus), chickens, and sea urchins, producing "morphant" embryos. With suitable cytosolic distribution systems, morpholines are effective in cell culture.

Morpholines have been developed as drugs under the name "NeuGenes" by AVI BioPharma Inc. They have been used in mammals, ranging from mice to humans, and some are currently being tested in clinical trials.

Bound to the 5' non-translated region of a messenger RNA (mRNA), the morpholines can interfere with the progression of the ribosome initiation complex from the 5' cap to the start codon. This prevents translation of the encoding region of the target transcript (called "silencing" gene expression). Morpholines provide a suitable medium for silencing expression of the protein and learning how this decrease changes cells or organisms. Some morpholines silence expression so effectively that after degradation of the pre-existing proteins, the target proteins become undetectable by Western blotting.

Morpholines can also interfere with the steps for processing the pre-mRNA, typically preventing RNPnp complexes which direct splicing from binding to their targets in the intron borders in a preRNA helix. Preventing U1 binding (on the donor side) or U2/U5 binding (in the polypyrimidine group and accepting site) can cause modified splicing, typically leading to the exclusion of mature mRNA exons. Directing some splicing targets causes the inclusion of introns, while the activation of cryptic splicing sites can lead to partial inclusions or exclusions. The U11/U12 RNPnp targets can also be blocked. The modification of the splicing can be suitably assayed by means of reverse transcriptase-polymerase chain reaction (RT-PCR) and it is seen as a migration in the band after gel electrophoresis of the RT-PCR products.

Morpholines have also been used to block miRNA activity, ribozyme activity, intron splicing silencers, and splicing enhancers. The functions of U2 and U12 RNPnp have been inhibited with morpholines. Morpholines directed against "slippery" RNA sequences within the encoding regions of proteins can induce changes in the reading frame of the translation. The activities of morpholines against this variety of targets suggest that morpholines can be used as a general multipurpose tool for blocking interactions of proteins or nucleic acids with mRNA.

Examples of LIF-specific antisense oligonucleotides are described in Kamohara et al., (Int J Oncol, 2007, 30:977-983) and Cheng et al. (Biol Reprod, 2004, 70:1270-1276).
DNA Enzymes Another aspect of the invention relates to the use of DNA enzymes to inhibit the expression of genes encoding the IL-6 type cytokine of the invention. The DNA enzymes incorporate some of the mechanistic characteristics of both antisense and ribozymes technologies. The DNA enzymes are designed such that they recognize a particular target nucleic acid sequence, similar to the antisense oligonucleotide, however like ribozymes, they are catalytic and specifically cleave the target nucleic acid.

There are currently two types of DNA enzymes, and both were identified by Santoro and Joyce (see, for example, U.S. Pat. No. 6,110,462). DNA enzyme 10-23 comprises a loop structure connecting two arms. The two arms provide specificity by recognizing a particular target nucleic acid sequence while the loop structure provides the catalytic function in physiological conditions.

Briefly, to design an ideal DNA enzyme which specifically recognizes and cleaves a target nucleic acid, the person skilled in the art must first identify the unique target sequence. This can be done using the same approach as that described for antisense oligonucleotides. Preferably, the unique or substantially unique sequence is rich in G/C of approximately 18 to 22 nucleotides. The high content in G/C helps in assuring a stronger interaction between the DNA enzyme and the target sequence.

When the DNA enzyme is synthesized, the specific antisense recognition sequence which will direct the enzyme to the messenger is divided such that it comprises the two arms of the DNA enzyme, and the loop of the DNA enzyme is located between the two specific arms.

Methods for making and administering DNA enzymes can be found, for example, in U.S. Pat. No. 6,110,462. Similarly, the methods for the delivery of DNA ribozymes in vitro or in vivo include the methods for the delivery of RNA ribozymes, as explained in detail above. Additionally, the person skilled in the art will recognize that, like the antisense nucleotide, DNA enzymes can optionally be modified to improve stability and to improve resistance to degradation.

Antisense RNA and DNA, ribozymes, iRNA and triple helix molecules of the invention can be prepared by means of any method known in the art for the synthesis of DNA and RNA molecules. These include methods for chemically synthesizing oligodeoxyribonucleotides and oligoribonucleotides well known in the state of the art, such as the chemical synthesis of phosphoramidite in solid phase, for example. Alternatively, the RNA molecules can be generated by means of in vitro and in vivo transcription of DNA sequences encoding the antisense RNA molecule. Such DNA sequences can be incorporated in a wide variety of vectors incorporating suitable RNA polymerase promoters, such as T7 or SP6 polymerase promoters. Alternatively, the antisense cDNA constructs constitutively or inducibly synthesizing antisense RNA, depending on the promoter used, can be stably introduced in cell lines. Furthermore, several well known modifications can be introduced in the nucleic acid molecules as a means to increase intracellular stability and half life. The possible modifications include but are not limited to the addition of flanking ribonucleotide or deoxyribonucleotide sequences at the 5' and/or 3' ends of the molecule or to the use of phosphorothioate or 2'-O-methyl bonds rather than phosphodiesterase in the backbone of the oligodeoxyribonucleotide.

Ribozymes

Ribozyme molecules designed to catalytically cleave transcripts of a target mRNA can also be used to prevent the translation of the mRNAs encoding the IL-6 type cytokine the activity of which is to be inhibited. Ribozymes are enzymatic RNA molecules capable of catalyzing specific RNA cleaving. (For a review, see, Rossi, Current Biology 4: 469-471, 1994). The mechanism of action of ribozyme involves sequence-specific hybridization of the ribozyme molecule to a complementary target RNA, followed by an endonucleolytic cleavage event. The composition of the ribozyme molecules preferably includes one or more sequences complementary to the target mRNA, and the well known sequence responsible for cleaving the mRNA or a functionally equivalent sequence (see U.S. Pat. No. 5,093, 245, for example, herein incorporated by reference in its entirety).

While ribozymes cleaving mRNA into site-specific recognition sequences can be used to destroy target mRNAs, the use of hammerhead ribozymes is preferred. Hammerhead ribozymes cleave the mRNA at locations commanded by the flanking regions forming complementary base pairs with those of the target mRNA. Preferably, the target mRNA has the following two base sequence: 5'-UG-3'. The construction and production of hammerhead ribozymes is well known in the art and fully described in Haseloff and Gerlach, Nature 334: 585-591, 1988; and see PCT application WO89/05852, the content of which is incorporated herein by reference. The sequences of the hammerhead ribozyme can be embedded in stable RNA, such as transfer RNA (tRNA) to increase the efficacy of the in vivo cleavage (Perriman et al., Proc. Natl. Acad. Sci. USA, 92: 6175-79, 1995; of Feyter, and Gaudron, Methods in Molecular Biology, Vol. 74, Chapter 43, "Expressing Ribozymes in Plants", Edited by Turner, P. C, Humana Press Inc., Totowa, N.J.). Particularly the expression of fusion ribozymes with tRNA mediated by RNA polymerase III is well known in the art (see, Kawasaki et al., Nature 393: 284-9, 1998; Kuwabara et al., Nature Biotechnol. 16: 961-5, 1998; and Kuwabara et al., Mol. Cell. 2: 617-27, 1998; Koseki et al., J Viral 73: 1868-77, 1999; Kuwabara et al., Proc Natl Acad Sci USA 96: 1886-91, 1999; Tanabe et al., Nature 406: 473-4, 2000). There is typically a number of potential cleavage sites of hammerhead ribozymes in a target cDNA sequence. The ribozyme is preferably manipulated such that the cleavage recognition site is located close to the 5' end of the target mRNA—to increase the efficacy and minimize intracellular accumulation of non-functional mRNA transcripts. Furthermore, the use of any cleavage recognition site located in the target sequence encoding different parts of C-terminal amino acid domains of, for example, short and long forms of the target, would allow selectively directing towards either form of the target, and thus having a selective effect on a form of the target gene product.

Ribozymes directed against genes necessarily contain a hybridization region complementary to two regions, each of at least 5 and preferably each of 6, 7, 8, 9, 10, 11, 12, 13, 14, 15, 16, 17, 18, 19 or 20 contiguous nucleotides in length of a target mRNA, such as an mRNA of a sequence represented in any of the human RAP80 proteins. Furthermore, ribozymes have very specific endonuclease activity which autocatalytically cleaves the encoding target mRNA. The present invention extends to ribozymes hybridizing with an encoding mRNA encoding a target gene such as a candidate target gene of a therapeutic drug, therefore hybridizing with the encoding mRNA and cleaving it, such that it is no longer capable of being translated for synthesizing a functional polypeptide product.

The ribozymes used in the compositions of the present invention also include endoribonuclease RNA (hereinafter "Cech-type ribozymes") such as that found naturally in Tetrahymena thermophila (known as IVS, or L-19 IVS RNA), which has been extensively described by Thomas Cech et al., (Zaug et al., Science 224:574-578, 1984; Zaug et al., Science 231: 470-475, 1986; Zaug et al., Nature 324: 429-433, 1986; international published patent application number WO88/04300 of University Patents Inc.; Been, et al., Cell 47: 207-216, 1986). Cech-type ribozymes have an active site with eight base pairs which hybridizes with a target RNA sequence, where the cleavage of the target RNA later takes place. The invention comprises those Cech-type ribozymes having as a target sequences having an active site with eight base pairs that are presented in a target gene or nucleic acid sequence.

The ribozymes can be formed by modified oligonucleotides (for example to improve stability, guidance, etc.) and they should be delivered to cells expressing the target gene in vivo. A preferred method for delivery involves using a DNA construct "encoding" the ribozyme under the control of a strong constitutive promoter of pol III or pol II, such that the transfected cells will produce sufficient amounts of the ribozyme to destroy the endogenous target messengers and inhibit translation. Since the ribozymes are catalytic, unlike other antisense molecules, lower intracellular concentration is required for them to be effective.

In certain embodiments, a ribozyme can be designed by first identifying a part of a sequence sufficient for causing a decreased efficacy by means of iRNA. The same part of the sequence can be later incorporated in a ribozyme. In this aspect of the invention, the parts of the ribozyme or iRNA which are directed against the genes are substantially the same sequence of at least 5 and preferably 6, 7, 8, 9.10, 11, 12, 13, 14, 15, 16, 17, 18, 19 or 20 or more contiguous nucleotides of a target nucleic acid, such as the nucleic acid of any of the human RAP80 sequences. In a long strand of target RNA, a significant number of target sites cannot be accessed by the ribozyme because they are hidden in the secondary and tertiary structures (Birikh et al., Eur J Biochem 245: 1-16, 1997). To overcome the problem of accessibility to the target RNA, computer-generated secondary structure predictions are typically used to identify the targets which will most likely be single-stranded or will have an "open" configuration (see Jaeger et al., Methods Enzymol 183: 281-306, 1989). Other approaches use a systematic approach to predict secondary structure which involve a large number of candidate oligonucleotides molecules to be hybridized (see Milner et al., Nat Biotechnol 15: 537-41, 1997; and Patzel and Sczakiel, Nat Biotechnol 16: 64-8, 1998). Additionally, U.S. Pat. No. 6,251,588, the content of which is herein incorporated by reference, describes methods for evaluating oligonucleotide probe sequences for predicting the potential for hybridizing a target nucleic acid sequence. The method of the invention provides the use of such methods for selecting preferred segments of a target mRNA sequence which is predicted to be single-stranded and, furthermore, for the opportunistic use thereof or a substantially identical target mRNA sequence, preferably comprising about 10-20 consecutive nucleotides of the target mRNA, in the design of both iRNA oligonucleotides and ribozymes of the invention.

Inhibitory Peptides

As it is used herein, the term "inhibitory peptide" relates to those peptides capable of binding to an IL-6 type cytokine and inhibiting its activity as has been explained above, i.e., preventing the IL-6 type cytokine from being able to induce the activation of the JAK-STAT signaling pathway.

An example of an inhibitory peptide are pegylated variants of LIF described in White et al. (J. Biol. Chem., 2007, Proc. Natl. Acad. Sci. USA, 104:19357-19362).

Inhibitors of Cytokine Receptor Binding

As it is used herein, the expression "inhibitors of cytokine receptor binding" indicates any compound which shows affinity for the IL-6 type cytokine and is therefore capable of sequestering the cytokine and preventing the binding thereof to its physiological receptors. The inhibitory polypeptide is preferably a soluble form of the IL-6 type cytokine receptor (the so-called decoy receptors). In the particular case of LIF, it is possible to use a soluble variant of the LIF receptor or the LIF binding protein (LBP), a soluble form of the alpha LIF receptor found naturally and which has been found to be capable of effectively preventing the effects of LIF on the metabolism of proteoglycans in joint cartilage explants (Bell et al., 1997, J. Rheumatol. 24:2394)

Inhibitory Antibodies

"Inhibitory antibody" is understood in the context of the present invention as any antibody which is capable of binding to an IL-6 type cytokine or to the receptors of said IL-6 type cytokines, preventing said IL-6 type cytokine from being able to induce the activation of the JAK-STAT signaling pathway. The antibodies can be prepared using any of the methods which are known for the person skilled in the art. Thus, polyclonal antibodies are prepared by means of immunization of an animal with the protein to be inhibited. Monoclonal antibodies are prepared using the method described by Kohler, Milstein et al. (Nature, 1975, 256: 495). Once antibodies with IL-6 type cytokine binding capacity or with the capacity to bind to the receptors of said cytokines are identified, those which are capable of inhibiting the activity of this protein will be selected using the assay for the identification of inhibitory agents described above (Metz, 2007 mentioned above).

Therefore, in a more particular embodiment, the antibodies are inhibitory antibodies specific to said IL-6 type cytokines or antibodies blocking the IL-6 type cytokine receptors.

Antibodies specific to LIF are described in U.S. Pat. No. 5,654,157A, Kim et al., (J. Immunol. Meth., 156: 9-17, 1992), Alphonso et al., (J. Leukocyte Biology (Abstracts of the 28th National Meeting of the Society for Leukocyte Biology, vol. 0, no. SP. 2 (1991) (NY, N.E., p. 49) (Mabs D4.16.9, D25.1.4, and D62.3.2).

In the present invention, the term "antibody" must be interpreted broadly and it includes polyclonal, monoclonal, multispecific antibodies and fragments thereof (F(ab')2, Fab), etc. provided they are capable of specifically recognizing the antigen of interest, which in the context of the present invention is an IL-6 type cytokine or the receptors of said IL-6 type cytokines. Examples of antibodies that can be used in the context of the present invention are, as non-limiting examples, polyclonal antibodies, monoclonal antibodies, recombinant antibodies, chimeric antibodies, humanized antibodies, completely human antibodies, etc.

The polyclonal antibodies are originally heterogeneous mixtures of antibody molecules produced in the serum of animals that have been immunized with an antigen. They also include monospecific polyclonal antibodies obtained from the heterogeneous mixtures, for example, by means of column chromatography with peptides of a single epitope of the antigen of interest.

A monoclonal antibody is a homogenous population of antibodies specific for a single epitope of the antigen. These monoclonal antibodies can be prepared by means of conventional techniques already described, for example in Köhler and Milstein [Nature, 1975; 256:495-397] or Harlow and Lane ["Using Antibodies. A Laboratory Manual" of E.

Harlow and D. Lane, Editor: Cold Spring Harbor Laboratory Press, Cold Spring Harbor, N.Y.; 1998 (ISBN 978-0879695439)].

A chimeric antibody is a monoclonal antibody constructed by means of the cloning or recombination of antibodies from different animal species. In a typical but non-limiting configuration of the invention, the chimeric antibody includes part of a monoclonal antibody, generally the variable fragment (Fv) including the sites for antigen recognition and binding, and the other part corresponding to a human antibody, generally the part including the constant region and the adjacent constant region.

A completely human antibody is an antibody or antibodies which have been produced in transgenic animals with a human immune system or by in vitro immunization of human immune cells (including both genetic and traditional immunization with or without adjuvants and pure or non-pure antigen; or by means of any method of exposure of the antigen to the immune system) or by means of native/synthetic libraries produced from human immune cells. These antibodies can be obtained and selected from transgenic animals (for example mice) in which human immunoglobulin genes have been cloned and which are immunized with the target antigen (in the present invention said antigen is an IL-6 type cytokine or the receptors of said IL-6 type cytokines). These antibodies can be obtained by selecting human single-chain variable fragments (scFv) or antigen binding fragments (Fab) presented in phage displays and subsequent cloning and grafting in a human antibody or by means of any other production and display method known by the person skilled in the art, of the libraries generated by cloning the variable fragments of both strands and subsequent combination/mutation thereof to generate the antibody libraries.

A humanized antibody is a monoclonal antibody constructed by means of the cloning and grafting of the hypervariable complementarity determining regions (CDR) of a murine monoclonal antibody in a human antibody in replacement of their own hypervariable CDR regions.

In addition, in the context of the present invention, the term "antibody" also includes variants with an altered glycosylation pattern, as well as glycosylated or non-glycosylated antibody fragments, obtained from the protein or by means of recombinant technology, which can consist of (i) variable zones of the antibodies bound to one another by a binding peptide (scFv), (ii) the variable zone together with the CH1 constant of the heavy chain (Fd) bound to the light chain by means of cysteines or by means of binding peptides and disulfide bond (scFab), (iii) new variants, such as single heavy chains, or (iv) any modification made to the antibody fragments for the purpose of making them more similar, less immunogenic (humanized) or more stable in biological fluids and which in the context of the present invention, have the capacity to prevent IL-6 type cytokines from performing their function (activity), i.e., inducing the activation of the JAK-STAT signaling pathway.

As the person skilled in the art will understand, the antibodies can be obtained by means of conventional genetic engineering or recombinant techniques, antibody production techniques, techniques for extraction and purification from biological fluids or tissues, or by any other conventional technique for obtaining proteins and antibodies which are widely known by the person skilled in the art. Illustrative non-limiting examples of techniques for the production of antibodies are: immunization techniques in animals, including transgenic animals for human immunoglobulin genes, production of monoclonal antibodies by means of hybridomas, production by means of antibody libraries, which can be native, synthetic or derived from organisms immunized against the antigen of interest and which could be selected by means of very different display methods (phage display, ribosome display, etc.) and subsequently, by means of genetic engineering techniques they could be redesigned and expressed in vectors designed for the production of recombinant antibodies of different sizes, composition and structure. A review of the main methods for the production and purification of antibodies can be found, for example, in:

"Handbook of Therapeutic Antibodies", by S. Dübel. Editor: Wiley-VCH, 2007, Vol: I to III (ISBN 978-3527314539);

"Antibodies: Volume 1: Production and Purification" by G. Subramanian Ed., Editor: Springer, 1st Ed, 2004 (ISBN 978-0306482458);

"Antibodies: Volume 2: Novel Technologies and Therapeutic Use", by G. Subramanian Ed., Editor: Springer, first edition, 2004 (ISBN 978-0306483158);

"Molecular Cloning: a Laboratory manual", by J. Sambrook and D. W. Russel Eds., Publisher: Cold Spring Harbor Laboratory Press, third edition, 2001 (ISBN 978-0879695774).

Other Compounds Inhibiting the Activity of an IL-6 Type Cytokine

Other compounds with the capacity to inhibit the expression of an IL-6 type cytokine include aptamers and spiegelmers, which are single- or double-stranded D or L nucleic acids which bind specifically to the protein resulting from a modification of the biological activity thereof. Aptamers and spiegelmers have a length of between 15 and 80 nucleotides, and preferably between 20 and 50 nucleotides.

Polypeptides with Inhibitory Activity of IL-6 Type Cytokines

Specifically, antagonists of LIF (an IL-6 type cytokine) which could be useful in the context of the present invention are:

LIF variants presenting mutations in receptor binding sites which show a reduced affinity for same or which are capable of binding to only one of the chains of the receptor. Examples of said mutants include:

the mutants described by Hudson et al., (J. Biol. Chem., 1996, 271:11971-11978), the LIF variants described in WO05030803 which have one or more mutations selected from the group of Q29A, G124R and N128A and which show a reduced affinity for the LIF receptor and for gp130. A high potency antagonist of LIF is the variant comprising MH35–BD/Q29A+G124R described by Fairlie, W. D. et al., (J. Biol. Chem., 2004, 279:2125-2134).

The mutants described in WO9601319 characterized by having one or more substitutions in the receptor binding regions and, specifically, at positions 25-38, 150 to 160 or 161 to 180 with respect to the numbering of human LIF.

Soluble variants of the LIF receptor based on the primary structure and with the capacity of binding to LIF and preventing it from interacting with its native receptor on the cell surface, such as fusion proteins comprising part of the extracellular region of the LIF receptor and the gp130 ligand binding domain, as described by Metz; S. et al. (J. Biol. Chem., 2008, 283:5985-5995).

As expressed at the beginning of the description, the inventors have opened a new therapeutic window in the treatment of diseases associated with unwanted cell proliferation, such as cancer, especially for the treatment of cancer caused by high activity the JAK-STAT signaling pathway, with the invention herein described.

In the context of the present invention, a "disease associated with unwanted cell proliferation" includes the growth, progression and the metastasis of cancer and tumors. Examples of diseases associated with unwanted cell proliferation which can be treated according to the methods described in the present invention are cancer, restenosis, arteriosclerosis, angiogenic diseases, fibrosis, dermatological diseases and inflammatory diseases.

In a particular embodiment of the invention, the disease associated with unwanted cell proliferation is cancer.

The terms "cancer" and "tumor" relate to the physiological condition in mammals characterized by the deregulated cell growth. The compounds of the present invention are useful for the treatment of breast, heart, lung, small intestine, colon, spleen, kidney, bladder, head, neck, ovarian, prostate, brain, pancreatic, skin, bone, bone marrow, blood, thymus, uterine, testicular and liver tumors. Particularly, tumors which can be treated with the compounds of the invention include adenoma, angiosarcoma, astrocytoma, epithelial carcinoma, germinoma, glioblastoma, glioma, hemangioendothelioma, hemangiosarcoma, hematoma, hepatoblastoma, leukemia, lymphoma, medulloblastoma, melanoma, neuroblastoma, osteosarcoma, retinoblastoma, rhabdomyosarcoma, sarcoma and teratoma. Particularly, the tumor/cancer is selected from the group of acral lentiginous melanoma, actinic keratosis, adenocarcinoma, adenoid cystic carcinoma, adenomas, adenosarcoma, adenosquamous carcinoma, astrocytic tumors, Bartholin gland carcinoma, basal cell carcinoma, bronchial gland carcinoma, capillary carcinoid, carcinoma, carcinosarcoma, cholangiocarcinoma, chondrosarcoma, cystadenoma, endodermal sinus tumor, endometrial hyperplasia, endometrial stromal sarcoma, endometrioid adenocarcinoma, ependymal sarcoma, Swing's sarcoma, focal nodular hyperplasia, gastronoma, germ line tumors, glioblastoma, glucagonoma, hemangioblastoma, hemangioendothelioma, hemangioma, hepatic adenoma, hepatic adenomatosis, hepatocellular carcinoma, insulinite, intraepithelial neoplasia, intraepithelial squamous cell neoplasia, invasive squamous cell carcinoma, large cell carcinoma, liposarcoma, lymphoblastic leukemia, lymphocytic leukemia, leiomyosarcoma, melanoma, malignant melanoma, malignant mesothelial tumor, nerve sheath tumor, medulloblastoma, medulloepithelioma, mesothelioma, mucoepidermoid carcinoma, myeloid leukemia, neuroblastoma, neuroepithelial adenocarcinoma, nodular melanoma, osteosarcoma, ovarian carcinoma, papillary serous adenocarcinoma, pituitary tumors, plasmacytoma, pseudosarcoma, pulmonary blastoma, renal cell carcinoma, retinoblastoma, rhabdomyosarcoma, sarcoma, serous carcinoma, squamous cell carcinoma, small cell carcinoma, soft tissue carcinoma, somatostatin secreting tumor, squamous carcinoma, squamous cell carcinoma, undifferentiated carcinoma, uveal melanoma, verrucous carcinoma, vagina/vulva carcinoma, VIPpoma, Wilm's tumor. Even more preferably, the tumor/cancer to be treated with the compounds of the invention includes brain cancer, head and neck cancer, colorectal carcinoma, acute myeloid leukemia, pre-B-cell acute lymphoblastic leukemia, bladder cancer, astrocytoma, preferably grade II, III or IV astrocytoma, glioblastoma, preferably glioblastoma multiforme, small cell cancer, and non-small cell cancer, preferably non-small cell lung cancer, metastatic melanoma, androgen-independent metastatic prostate cancer, androgen-dependent metastatic prostate cancer and breast cancer, preferably breast ductal cancer or breast carcinoma.

In a particular embodiment of the invention, the cancer or the cells forming the tumors occurring in the cancer is characterized by presenting high levels of the IL-6 type cytokine. In the context of the present invention, with "high levels" of an IL-6 type cytokine, it is understood that the concentrations of the cytokine are greater than those occurring in a control sample by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150% or more.

Control sample is understood as a sample having levels of cytokine type IL-6 which are used as a reference for the determination of the relative levels of said cytokine in a test sample. The reference samples are typically obtained from patients who are well documented from the clinical point of view, and who present no disease. In said samples, the biomarker concentration can be determined, for example, by means of the determination of the average concentration in a reference population. In the determination of the reference concentration for a certain marker, it is necessary to take such as age, gender, the physical state and the like of the patient. For example, the reference sample can be obtained from identical amounts of a group of at least 2, at least 10, at least 100 to more than 1000 individuals, such that the population is statistically significant.

The concentration of IL-6 type cytokine can be determined intracellular, in the interstitial gap or in extracts in which both the intracellular protein and the one found in the interstitial gap. The levels of IL-6 cytokine can be determined by means of measuring the activity of said cytokine using assays suitable for that purpose, or by means of measuring the amount of protein using immunological methods or by means of measuring the mRNA corresponding to the IL-6 type cytokine.

In another particular embodiment, the cancer is caused by high activity of the JAK-STAT signaling pathway which, in another even more particular embodiment, is a glioma, preferably grade IV glioma.

As previously mentioned, the inhibitory agent of the invention is capable of inhibiting the proliferation of tumor stem cells, such that its use is particularly useful for the treatment of diseases that can benefit from inhibition of the proliferation of stem cells. Thus, in a preferred embodiment, the inhibitory agents act through the self-regeneration of tumor stem cells.

The term "arteriosclerosis" relates to the thickening and hardening or the arterial wall. A specific type of arteriosclerosis is atherosclerosis, which is the cause of most coronary artery diseases, of aortic aneurysm and of arterial disease of the lower limbs, and it furthermore contributes to cerebrovascular disease. A normal artery typically has an inner part (the intima) formed by a single layer of endothelial cells. Overlaid on this layer is the so-called middle layer containing only smooth muscle cells. The outer layer, in turn, is the adventitia. With aging, the width of the intima continuously increases partly as a result of the migration and proliferation of the smooth muscle cells. A similar increase also occurs in the width of the intima as a result of several traumatic episodes or interventions, such as those occurring when a dilation process causes damage to the wall of the vessels. The compounds used in the present invention are potentially useful for inhibiting the proliferation of endothelial cells, smooth muscle cells and fibroblasts. Accordingly, the labdane-type diterpenoid compounds described in the invention can also be used for the treatment of arteriosclerotic conditions. "Arteriosclerotic conditions" are understood as classic atherosclerosis, accelerated atherosclerosis and any other arteriosclerotic condition characterized by unwanted proliferation of endothelial and/or smooth vascular muscle cells, including vascular complications from diabetes and diabetic glomerulosclerosis.

The term "restenosis" is understood as that disease presenting excessive proliferation and migration of cells as a result of the release of growth factors caused by mechanical damage to the endothelial cells forming the coronary arteries.

"Angiogenic disease" is understood as a disease or medical condition presenting abnormal neovascularization. Such diseases or conditions include diabetic retinopathy, neovascular glaucoma, rheumatoid arthritis and some cancers, such as hemangioendotheliomas, hemangiomas and Kaposi's sarcoma. The proliferation of endothelial cells and of smooth vascular muscle cells is the main characteristic of neovascularization. The compounds described in the present invention are useful for inhibiting said proliferation and, accordingly, for inhibiting the progression of the angiogenic condition which depends all or in part on said neovascularization.

The term "fibrosis" relates to a formation or excessive development of fibrous connective tissue in an organ or tissue. Fibrosis includes, for example, endomyocardial fibrosis, idiopathic pulmonary fibrosis, emphysema, pulmonary fibrosis (leading to a chronic obstructive pulmonary disease), Peyronie's disease, scleroderma, diffuse parenchymal lung disease, keloids, mediastinal fibrosis, progressive massive fibrosis, proliferative fibrosis, neoplastic fibrosis, interstitial renal fibrosis, hepatic fibrosis, surgical scars or burns.

The term "dermatological diseases" is understood as diseases of the skin presenting cell proliferation associated with any proliferative dysfunction. These dysfunctions include, for example, keloids, hypertrophic burn scars, seborrheic keratosis, papilloma virus infection, actin keratosis and eczema.

The term "inflammatory diseases" is understood as diseases causing inflammation as the result of cell proliferation associated with any proliferative dysfunction. They include, for example, proliferative glomerulonephritis, lupus erythematosus, scleroderma, temporary arthritis, thromboangiitis and mucocutaneous lymph node syndrome.

In another aspect, the invention relates to a pharmaceutical composition comprising a therapeutically effective amount of an inhibitory agent according to the present invention together with a pharmaceutically acceptable carrier for the treatment of diseases associated with unwanted cell proliferation. Examples of diseases associated with unwanted cell proliferation have been mentioned above in the specification.

In the context of the present invention, "therapeutically effective amount" is understood as the amount of agent inhibiting the expression and/or activity of an IL-6 type cytokine that is necessary to achieve the desired effect which, in this specific case, is the treatment of diseases associated with unwanted cell proliferation. Generally, the therapeutically effective amount of the inhibitory agent according to the present invention to be administered will depend, among other factors, on the individual to be treated, on the severity of the disease said individual suffers, on the chosen dosage form, etc. For this reason, the doses mentioned in this invention must be considered only as a guideline for the person skilled in the art, and the latter must adjust the doses according to the previously mentioned variables. Nevertheless, an inhibitory agent according to the present invention can be administered one or more times a day, for example, 1, 2, 3 or 4 times a day, in a typical total daily amount comprised between 0.1 and 1000 mg/kg body mass/day, preferably 10 mg/kg body mass/day.

In the context of this specification, the term "treatment" or "treating" means the administration of an inhibitory agent according to the invention to prevent, relieve or eliminate the disease or one or more symptoms associated with said disease associated with unwanted cell proliferation. "Treatment" also includes preventing, relieving or eliminating the physiological sequelae of the disease. In the context of this invention, the term "relieve" is understood to mean any improvement of the situation of the treated patient—both subjectively (feelings of or about the patient) and objectively (measured parameters).

The term "vehicle, adjuvant and/or carrier" relates to molecular entities or substances with which the active ingredient is administered. Such pharmaceutical vehicles, adjuvants or carriers can be sterile liquids, such as waters and oils, including those of petroleum or of an animal, plant or synthetic origin, such as peanut oil, soybean oil, mineral oil, sesame oil and the like, excipients, disintegrating agents, wetting agents or diluents. Suitable pharmaceutical carriers are described in "Remington's Pharmaceutical Sciences" by E. W. Martin.

In the context of the present invention, the term "pharmaceutically acceptable" relates to molecular entities and compositions which are physiologically tolerable and do not typically cause an allergic reaction or a similar adverse reaction, such as gastric disorder, dizziness and the like, when they are administered to a human. The term "pharmaceutically acceptable" preferably means approved by a federal or state government regulatory agency, or included in the US Pharmacopoeia or other generally recognized pharmacopoeia for use in animals, and more particularly in humans.

The inhibitory agent of the expression and/or the activity of an IL-6 type cytokine, as well as the pharmaceutical compositions containing them, can be used together with other additional drugs useful in the treatment of diseases associated with unwanted cell proliferation. Said additional drugs can form part of the same pharmaceutical composition or they can alternatively be provided in the form of a separate composition for their administration that may or may not be simultaneous to that of the pharmaceutical composition comprising said inhibitory agent of the expression and/or the activity of an IL-6 type cytokine.

Examples of other additional drugs useful in the treatment of diseases associated with unwanted cell proliferation include but are not limited to alkylating agents such as, for example, cyclophosphamide, carmustine, daunorubicin, mechlorethamine, chlorambucil, nimustine, melphalan and the like; anthracyclines, such as, for example, daunorubicin, doxorubicin, epirubicin, idarubicin, mitoxantrone, valrubicin and the like; taxane compounds, such as, for example, paclitaxel, docetaxel and the like; topoisomerase inhibitors such as, for example, etoposide, teniposide, tuliposide, irinotecan and the like; nucleotide analogs such as, for example, azacitidine, azathioprine, capecitabine, cytarabine, doxifluridine, fluorouracil, gemcitabine, mercaptopurine, methotrexate, thioguanine, ftorafur and the like; platinum-based agents such as, for example, carboplatin, cisplatin, oxaliplatin and the like; antineoplastic agents such as, for example, vincristine, leucovorin, lomustine, procarbazine and the like; hormone modulators such as, for example, tamoxifen, finasteride, 5-α-reductase inhibitors and the like; vinca alkaloids such as, for example, vinblastine, vincristine, vindesine, vinorelbine and the like. Suitable chemotherapy agents are described in more detail in the literature, such as in The Merck Index in CD-ROM, 13$^{th}$ edition.

The pharmaceutical composition of the invention can be administered by any suitable administration route, for example, oral, parenteral (for example, subcutaneous, intraperitoneal, intravenous, intramuscular, etc.), rectal, etc., typically, by oral route due to the chronic nature of the disease to be treated.

Illustrative examples of pharmaceutical dosage forms administered by oral route include tablets, capsules, granulates, solutions, suspensions, etc., and they can contain conventional excipients, such as binders, diluents, disintegrating agents, lubricants, wetting agents, etc., and can be prepared by conventional methods. The pharmaceutical compositions can also be suitable for their parenteral administration, in the form of, for example, sterile solutions, suspensions or lyophilized products, in the suitable dosage form; in this case, said pharmaceutical compositions will include the suitable excipients, such as buffers, reagents, etc. In any case, the excipients will be chosen according to the chosen pharmaceutical dosage form.

A review of the different pharmaceutical dosage forms of drugs and of their preparation can be found in the book "*Tratado de Farmacia Galénica*", by C. Faulí i Trillo, 10$^{th}$ Edition, 1993, Luzán 5, S. A. de Ediciones.

As the person skilled in the art will understand, when the inhibitory agent of the expression and/or the activity of an IL-6 type cytokine according to the invention comprises a nucleotide sequence, such as for example, antisense oligonucleotides, interference RNAs (siRNAs), catalytic RNAs or specific ribozymes, RNA with decoy activity, etc., the pharmaceutical composition of the invention can be formulated in the form of a composition intended for its use in gene therapy; by way of non-limiting illustration, in this case, the pharmaceutical composition of the invention can contain a viral or non-viral vector, comprising said nucleotide sequence or a gene construct comprising the mentioned sequence. By way of non-limiting illustration, said vectors can be viral vectors, for example, based on retroviruses, adenoviruses, etc., or non-viral such as DNA-liposome, DNA-polymer, DNA-polymer-liposome complexes, etc. [see "Nonviral. Vectors for Gene Therapy", edited by Huang, Hung and Wagner, Academic Press (1999)]. Said vectors can be administered directly to the human or animal body by conventional methods and they can alternatively be used to transform, transfect or infect cells, for example, mammal cells, including human cells, ex vivo, and subsequently implant them in the human or animal body to obtain the desired therapeutic effect. For their administration to the human or animal body, said cells will be formulated in a suitable medium that does not adversely affect the viability of said cells.

Screening Methods of the Invention

The finding made by the authors of the present invention and described in the present specification not only applies in the treatment of diseases associated with unwanted cell proliferation or the diagnosis of said diseases, but also the involvement of LIF in the activation of the JAK/STAT cascade can also be used in the development a screening method for the identification of compounds capable of blocking/inhibiting the cell proliferation of tumor cells induced by an IL-6 type cytokine or a functionally equivalent variant thereof.

Therefore, in another aspect, the invention relates to an in vitro method for the identification of compounds capable of blocking/inhibiting the cell proliferation of tumor cells induced by an IL-6 type cytokine or a functionally equivalent variant thereof comprising the steps of:

(i) contacting a cell expressing the receptor for an IL-6 type cytokine with an IL-6 type cytokine and a candidate compound, and (ii) identifying those compounds blocking the cell proliferation of said cell.

In a first step, the method of the invention involves contacting a cell expressing the receptor for an IL-6 type cytokine with an IL-6 type cytokine with the presence of a candidate compound in any degree of purity.

In the context of the present invention, "cell" is understood as any cell expressing a receptor for an IL-6 type cytokine. Cells in which receptors of IL-6 type cytokines are expressed and which can be used in the methods of the present invention include cells derived from solid tumors, such as breast cancer cells, bladder cancer cells, melanoma cells, ovarian cancer cells, pancreatic cancer cells, prostate cancer cells, colon cancer cells, lung cancer cells and the like, as well as cells derived from liquid tumors, such as leukemia and lymphoma cells. In a particular embodiment, the cell expressing the receptor for an IL-6 type cytokine is a glioma cell, preferably, a glioma initiating cell (GIC).

Examples of receptors for IL-6 type cytokines can be found in Auernhammer and Melmed, 2000 (Endocrine reviews, vol. 21(3): 313-345), such as the LIF receptor (LIFR), Oncostatin M receptor (OMSR) etc. Thus, the cells object of study include higher eukaryotic cells, preferably mammal cells. Preferably, the cells which are used in the present invention are those in which the receptors for IL-6 type cytokines are constitutively expressed. Alternatively, conventional cell lines can also be used either directly if it is found that they suitable express the receptors for IL-6 type cytokines or after the prior transfection of DNA constructs which allow the expression of said receptors. Suitable cells for this purpose include cells of the CHO, VERO, BHK, HeLa, COS, MDCK 293, 3T3, WI38 lines and the like. In a preferred embodiment, the cell which is used in the method of the invention is a glioma cell, preferably, a grade IV glioma cell.

The person skilled in the art will observe that, depending on the type of receptors that are expressed in the cell used in the screening method of the invention, it will be necessary to use the corresponding cytokine. The cytokine is preferably selected from the group of LIF, IL-6, IL-11, oncostatin M, cardiotrophin-1, CNTF and CLC.

Contacting the cell with the candidate compound can be done using any method known for the person skilled in the art, including directly contacting the cell expressing the receptor for an IL-6 type cytokine, said cell being in culture, with the IL-6 type cytokine and the candidate compound in a solvent suitable for the interaction thereof, such as DMSO and the like.

According to the present invention, "contacting" a cell with the candidate compound includes any possible way of carrying the candidate compound to the proximity of its target cell, either on the surface of the cell or to the interior thereof. Thus, in the event that the candidate compound is a low molecular weight molecule, it is sufficient to add said molecule to the culture medium. In the event that the candidate compound is a high molecular weight molecule (for example, biological polymers such as a nucleic acid or a protein, antibodies or polypeptides), it is necessary to supply the means for this molecule to access the cell interior. In the event that the candidate molecule is a nucleic acid (for example, antisense oligonucleotides, interference RNAs (siRNAs), catalytic RNAs or specific ribozymes, RNA with decoy activity), conventional transfection methods can be used for the introduction of the DNA construct. In the event that the candidate compound is a protein, the cell can contact both with the protein directly and with the nucleic acid encoding it coupled to elements which allow its transcription/translation once they are in the cell interior. To that end, any of the previously mentioned methods can be used to allow its entry into the cell interior. Alternatively, it is possible to contact the cell with a variant of the protein to be studied which has been modified with a peptide capable of promoting the translocation of the protein to the cell interior, such as the Tat peptide derived from the HIV-1 TAT protein, the third helix of the homeodomain of the *D. melanogaster* Antennapedia protein, the herpes simplex virus VP22 protein and arginine oligomers (Lindgren, A. et al., 2000, *Trends Pharmacol. Sci*, 21:99-103, Schwarze, S. R. et al., 2000, *Trends Pharmacol. Sci.*, 21:46-48, Lundberg, M et al., 2003, *Mol. Therapy.* 8:143-150 and Snyder, E. L. and Dowdy, S. F., 2004, *Pharm. Res.* 21:389-393).

Preferably, the candidate compound is not isolated but rather forms part of a more or less complex mixture derived from a natural source, or it forms part of a library of compounds. Examples of libraries of compounds that can be assayed according to the method of the present invention include, but are not limited to, libraries of peptides including both peptides and peptide analogs comprising D-amino acids or peptides comprising non-peptide bonds, libraries of nucleic acids including nucleic acids with non-phosphodiester bonds of the phosphorothioate or peptide nucleic acid type, libraries of antibodies, of carbohydrates, of low molecular weight compounds, preferably organic molecules, of peptidomimetics, and the like. In the event that a library of low molecular weight organic compounds is used, the library could be pre-selected so that it contains compounds that can more readily access the cell interior. Thus, the compounds can be selected based on determined parameters such as size, lipophilicity, hydrophilicity, capacity of forming hydrogen bonds.

Alternatively, the candidate compounds can form part of an extract obtained from a natural source. The natural source can be animal, plant obtained from any environment, including but not limited to extracts of terrestrial, aerial, marine organisms and the like.

In a second step the invention comprises identifying those compounds blocking the cell proliferation of the cell expressing a receptor for an IL-6 type cytokine. Examples of methods suitable for detecting if cell proliferation has been blocked include but are not limited to:

Determining Telomerase Activity

The enzyme activity of the telomerase can be determined by means of any method known in the art. For example, the telomerase activity can be determined by means of determining the elongation rate of a certain repetitive sequence containing 2, 3 or more repetitions of the unitary telomere sequence (Yegorov, E. E. et al., 1997, Mol. Biol., 31:130-136). To measure said activity, cytoplasmic extracts, nuclear extracts, cell lysates or whole cells can be used. "Increase" in the telomerase activity is understood to mean that the absolute level of telomerase activity in a particular cell is increased compared with normal cells in the same individual or compared with normal cells in subjects who do not suffer the condition.

Determining the Length of the Telomeres

Methods for determining the length of the telomeres have been greatly described in the art by Harley, C. B., et al. (Nature, 1990, 345:458-460); Levy, M. Z. et al., (J. Mol. Biol., 1992, 225:951-960); Lindsey, J. et al., (Mutat. Res., 1991, 256:45-48) and Allsopp, R. C. et al., (Proc. Natl. Acad. Sci. USA, 1992, 89:10114-10118), among others. Restriction endonucleases which do not fragment the telomeric DNA are conventionally used to later separate the fragments obtained by their molecular weight and detect the telomeres by means of hybridization using probes specific for the sequence of the telomeres.

Determining Cell Proliferation

Cell proliferation can be determined by means of methods widely known for the person skilled in the art, including determining the cellular duplication time, as described by Harley et al., (Nature, 1990, 345:458-460). The cell proliferation rate can be determined by means of determining the incorporation of tritiated uridine in the cell or colorimetric assays using BrdU.

In the present invention, "functionally equivalent variant of an IL-6 type cytokine" is understood as a protein the amino acid sequence of which (i) is substantially homologous to the amino acid sequence of an IL-6 type cytokine and (ii) performs the same functions as said IL-6 type cytokine. The functional similarity of a protein with another specific one can be determined by means of interference assays with the expression of the gene encoding the specific protein which, upon reducing expression, would reduce the activity of that protein, and the subsequent recovery of the activity by means of expressing the sequence of the other protein. These experiments are performed using interference RNA sequences specific and complementary for the sequence of the specific protein and expression vectors incorporating the sequence specific of the other protein regulated by an inducible promoter or not.

An amino acid sequence is substantially homologous to a certain amino acid sequence when it has a degree of identify of at least 70%, advantageously at least 75%, typically at least 80%, preferably at least 85%, more preferably at least 90%, even more preferably at least 95%, 97%, 98% or 99%, with respect to said certain amino acid sequence. The degree of identify between two amino acid sequences can be determined by conventional methods, for example, by means of standard sequence alignment algorithms known in the state of the art, such as, for example BLAST [Altschul S. F. et al. Basic local alignment search tool. J Mol Biol. 1990 Oct. 5; 215(3):403-10].

The person skilled in the art understands that the mutations in the nucleotide sequence of the gene encoding an IL-6 type cytokine giving rise to conservative substitutions of amino acids at non-critical positions for the functionality of the protein are evolutionarily neutral mutations that do not affect their overall structure global or functionality. Said variants fall within the scope of the present invention. Those functionally equivalent variants of an IL-6 type cytokine having insertions, deletions or modifications of one or more amino acids with respect to said IL-6 type cytokine and, furthermore conserve the same functions as said cytokine, are also included within the scope of the invention.

Therefore, as it is used herein the term "functionally equivalent variant" also includes any functionally equivalent fragment of an IL-6 type cytokine. The term "fragment" relates to a peptide comprising a portion of a protein. In this case, a functionally equivalent fragment of an IL-6 type cytokine is a peptide or protein comprising a portion of an IL-6 type cytokine and the same functions as said cytokine.

Diagnostic Methods of the Invention

The authors of the present invention have shown that an IL-6 type cytokine, more specifically LIF, is involved in the activation of the JAIL-STAT cascade, thus inducing the cell proliferation process and the increase of tumor stem cells (cancer stem cells). This finding allows developing diagnostic methods for diagnosing diseases associated with unwanted cell proliferation based on determining the levels of IL-6 type cytokine.

Thus, in another aspect, the invention relates to an in vitro method for the diagnosis of diseases associated with unwanted cell proliferation in a subject or for determining the predisposition of a subject to suffer said disease associated with unwanted cell proliferation, or for determining the stage or severity of said disease associated with unwanted cell proliferation in a subject, or for monitoring the effect of the therapy administered to a subject with said disease associated with unwanted cell proliferation, which comprises quantifying the expression levels of the gene encoding an IL-6 type cytokine or of the protein encoded by said gene or functionally equivalent variant of said protein in a biological sample from said subject, wherein an increase of the expression of the gene encoding an IL-6 type cytokine or of the protein encoded by said gene or functionally equivalent variant of said protein, with respect to the expression of the gene encoding an IL-6 type cytokine or of the protein encoded by said gene or functionally equivalent variant of said protein in a control sample, is indicative of a disease associated with unwanted cell proliferation, or of a greater predisposition of said subject to suffer from a disease associated with unwanted cell proliferation or of the non-response to the therapy administered to said subject.

As used herein, diagnosing relates to evaluating the probability according to which a subject suffers from a disease. As will be understood by the persons skilled in the art, such evaluation normally may not be correct for 100% of the subjects to be diagnosed, although it is preferably is. However, the term requires being able to identify a statistically significant part of the subjects as suffering the disease or having a predisposition to same. The person skilled in the art can determine if a part is statistically significant by simply using several well known statistical evaluation tools, for example, determination of confidence intervals, determination of the p-value, Student's t-test, Mann-Whitney test, etc. The details are in Dowdy and Wearden, Statistics for Research, John Wiley & Sons, New York 1983. The preferred confidence intervals are at least 50%, at least 60%, at least 70%, at least 80%, at least 90%, at least 95%. The p-values are preferably 0.2, 0.1, 0.05.

As used herein, the term "predisposition" means that a subject has still not developed the disease or any of the symptoms of the disease mentioned above or other diagnostic criteria but will, however, develop the disease in the future with a certain probability. Said probability will be significantly different from the statistical probability of onset of a disease associated with unwanted cell proliferation. It is preferably diagnosed that the probability of developing a disease associated with unwanted cell proliferation is at least 30%, at least 40%, at least 50%, at least 60%, at least 70%, at least 80%, at least 90% or 100% of a predisposition. The diagnosis of a predisposition can sometimes be referred to as prognosis or prediction of the probability of a subject developing the disease.

In the context of the present invention, "control sample" is understood as the reference sample which is used to determine the variation of the expression levels of the genes and proteins used in the present invention. In an embodiment, the reference value is obtained from the provided signal using a sample of tissue obtained from a healthy individual. Preferably, samples are taken from the same tissue of several healthy individuals and combined, such that the amount of mRNA or of polypeptides in the sample reflects the mean value of said molecules in the population.

The quantification of the expression levels of a gene encoding an IL-6 type cytokine can be performed from the RNA resulting from the transcription of said gene (mRNA) or, alternatively, from the complementary DNA (cDNA) of said gene. Additionally, the method of the invention can include performing a step of extraction for the purpose of obtaining the total RNA, which can be performed by means of conventional techniques (Chomczynski et al., Anal. Biochem., 1987, 162:156; Chomczynski P., Biotechniques, 1993, 15:532).

Virtually any conventional method can be used within the context of the invention to detect and quantify the levels of mRNA encoded by a gene encoding an IL-6 type cytokine or of its corresponding cDNA. By way of non-limiting illustration, the levels of mRNA encoded by said gene can be quantified by means of using conventional methods, for example, methods comprising the amplification of the mRNA and the quantification of the product of the amplification of said mRNA, such as electrophoresis and staining, or alternatively, by means of Northern blot and the use of probes specific for the mRNA of the genes of interest or of their corresponding cDNA, mapping with the S1 nuclease, RT-LCR, hybridization, microarrays, etc., preferably, by means of quantitative real-time PCR using suitable sets of probes and primers. Similarly, the levels of the cDNA corresponding to said mRNA encoded by the gene encoding an IL-6 type cytokine can also be quantified by means of using conventional techniques; in this case, the method of the invention includes a step of synthesis of the corresponding cDNA by means of reverse transcription (RT) of the corresponding mRNA followed by amplification and quantification of the product of the amplification of said cDNA. Conventional methods for quantifying the expression levels can be found, for example, in Sambrook et al., 2001. "Molecular cloning: a Laboratory Manual", $3^{rd}$ ed., Cold Spring Harbor Laboratory Press, N.E., Vol. 1-3.

Thus, in a particular embodiment of the method of the invention, the quantification of the expression levels of the gene encoding an IL-6 type cytokine comprises the quantification of the messenger RNA (mRNA) of said gene, a fragment of said mRNA, complementary DNA (cDNA) of said gene, a fragment of said cDNA, or mixtures thereof.

In another particular embodiment, the quantification of the expression levels of the gene encoding an IL-6 type cytokine is performed by means of a quantitative polymerase chain reaction.

In addition, to put the method of the invention into practice, the expression levels of the protein encoded by said gene encoding an IL-6 type cytokine, i.e., a gene encoding IL-6, IL-11, leukemia inhibitory factor (LIF), oncostatin M (OSM), cardiotrophin-1 (CT-I), ciliary neurotrophic factor (CNTF) or cardiotrophin-like cytokine (CLC) can also be quantified.

As is understood by the person skilled in the art, the expression level of a protein can be quantified by means of any conventional method. By way of non-limiting illustration, the levels of protein can be quantified, for example, by means of the use of antibodies with the capacity to bind to said proteins (or to fragments thereof containing an antigenic determinant) and the subsequent quantification of the complexes formed. The antibodies which are used in these assays may or may not be labeled. Illustrative examples of markers which can be used include radioactive isotopes, enzymes, fluorophores, chemiluminescent reagents, enzyme substrates or cofactors, enzyme inhibitors, particles, dyes, etc. There is a large variety of known assays which can be used in the present invention which use non-labeled antibodies (primary antibody) and labeled antibodies (secondary antibody); these techniques include Western-blot, ELISA (enzyme-linked immunosorbent assay), RIA (radioimmunoassay), competitive EIA (competitive enzyme immunoassay), DAS-ELISA (double-antibody sandwich ELISA), immunocytochemical and immunohistochemical techniques, techniques based on the use of biochips or microarrays of proteins which include specific antibodies or assays based on colloidal precipitation in formats such as dipsticks. Other ways to detect and quantify proteins include affinity chromatography techniques, ligand binding assays, etc. In another particular embodiment, the quantification of the levels of protein is performed by means of Western blot, immunohistochemistry or ELISA.

In another preferred embodiment, the determination of the expression levels of the IL-6 type cytokine can be carried out by means of the determination of the activity of said protein, since high expression levels generally result in a higher specific activity of said protein in a sample. Assays for determining the activity of IL-6 type cytokines have been previously described in the context of the therapeutic methods of the invention.

The IL-6 type cytokines the levels of which can be used as markers of unwanted cell proliferation have been previously described in the present description and are applicable to the method of the invention. Likewise, the diagnostic method of the invention can be applied to any of the diseases associated with unwanted cell proliferation defined above. In a preferred embodiment, the disease associated with unwanted cell proliferation is a cancer, preferably a cancer having high levels of an IL-6 type cytokine or high activity of the JAK-STAT signaling pathway.

Putting the method of the invention into practice comprises obtaining a biological sample from the subject to be studied. Illustrative non-limiting examples of said samples include different types of biological fluids, such as blood, serum, plasma, cerebrospinal fluid, peritoneal fluid, faeces, urine and saliva, as well as samples of tissues. The samples of biological fluids can be obtained by any conventional method like the samples of tissues; by way of illustration said samples of tissues can be samples of biopsies obtained by surgical resection.

In another aspect, the invention relates to the use of a kit comprising reagents for the quantification of the expression levels of the gene encoding an IL-6 type cytokine or of the protein encoded by said gene or functionally equivalent variant of said protein for the diagnosis of cancer in a subject or for determining the predisposition of a subject to suffer said cancer, or for determining the stage or severity of said cancer in a subject, or for monitoring the effect of the therapy administered to a subject with said cancer, in which if the reagents detect an increase in the expression of said gene or said protein or functionally equivalent variant thereof with respect to a control sample, then said subject can suffer from a disease associated with unwanted cell proliferation, or present a greater predisposition to suffer said disease associated with unwanted cell proliferation, or present a greater severity of said disease, or the administered therapy is not being effective.

All the terms and expressions used in the definition of the use of the kit have been previously described and explained for other inventive aspects and particular embodiments of the present invention, and are also applicable to the use of the kit described herein.

Methods for Designing Customized Therapies and for Selecting Patients Who can Benefit from the Therapy Based on IL-6 Inhibitors The authors of the present invention have shown that inhibitors of cytokines belonging to the family IL-6 and, more particularly, LIF, caused an inhibition of the proliferation of tumor cells. They have likewise observed that there are tumors having very high levels of said cytokines, therefore they propose that the therapy based on the use of IL-6 inhibitors can be particularly beneficial for the treatment of patients in which there are high levels of IL-6 type cytokine.

Thus, in another aspect, the invention relates to an in vitro method for designing a customized therapy for a patient suffering from a disease associated with unwanted cell proliferation comprising:

(a) quantifying the expression levels of the IL-6 type cytokine in said patient, and (b) comparing said expression levels with control levels, wherein if the expression levels of an IL-6 type cytokine in said patient are greater than the control values, then an inhibitory agent of an IL-6 type cytokine is administered to said patient.

In another aspect, the invention relates to an in vitro method for selecting patients suffering from a disease associated with unwanted cell proliferation, to be treated with an inhibitory agent of an IL-6 type cytokine comprising a) quantifying the expression levels of the IL-6 type cytokine in said patient, and b) comparing said expression levels with control levels, wherein if the expression levels of an IL-6 type cytokine in said patient are greater than the control values, then said patient is selected to receive treatment with an inhibitory agent of an IL-6 type cytokine.

In both aspects, a preferred embodiment is that in which the disease associated with unwanted cell proliferation is associated with unwanted stem cell proliferation.

In a preferred embodiment, the inhibitory agent of an IL-6 type cytokine is selected from the group consisting of siRNAs, antisense oligonucleotides, specific ribozymes, antibodies and polypeptides. The inhibitory agents are preferably antibodies and, more preferably, inhibitory antibodies specific to said IL-6 type cytokine or antibodies blocking the IL-6 type cytokine receptors.

The IL-6 type cytokines which can be used as markers for selecting patients or for designing customized therapies have been described with detail above and are selected from LIF, IL-6, IL-11, oncostatin M, cardiotrophin-1, CNTF and CLC.

The diseases presenting unwanted cell proliferation are those described above. In a preferred embodiment, said disease presenting unwanted cell proliferation is cancer. Even more preferably, said cancer is caused by a high activity of the JAK-STAT signaling pathway.

In a preferred embodiment, said cancer is one of the following: glioma, pre-B cell acute lymphoblastic leukemia, acute myeloid leukemia, colorectal carcinoma, bladder cancer, breast ductal cancer or breast carcinoma. Even more preferably, said glioma is grade IV glioma.

Prognostic Methods of the Invention

Figure 12:
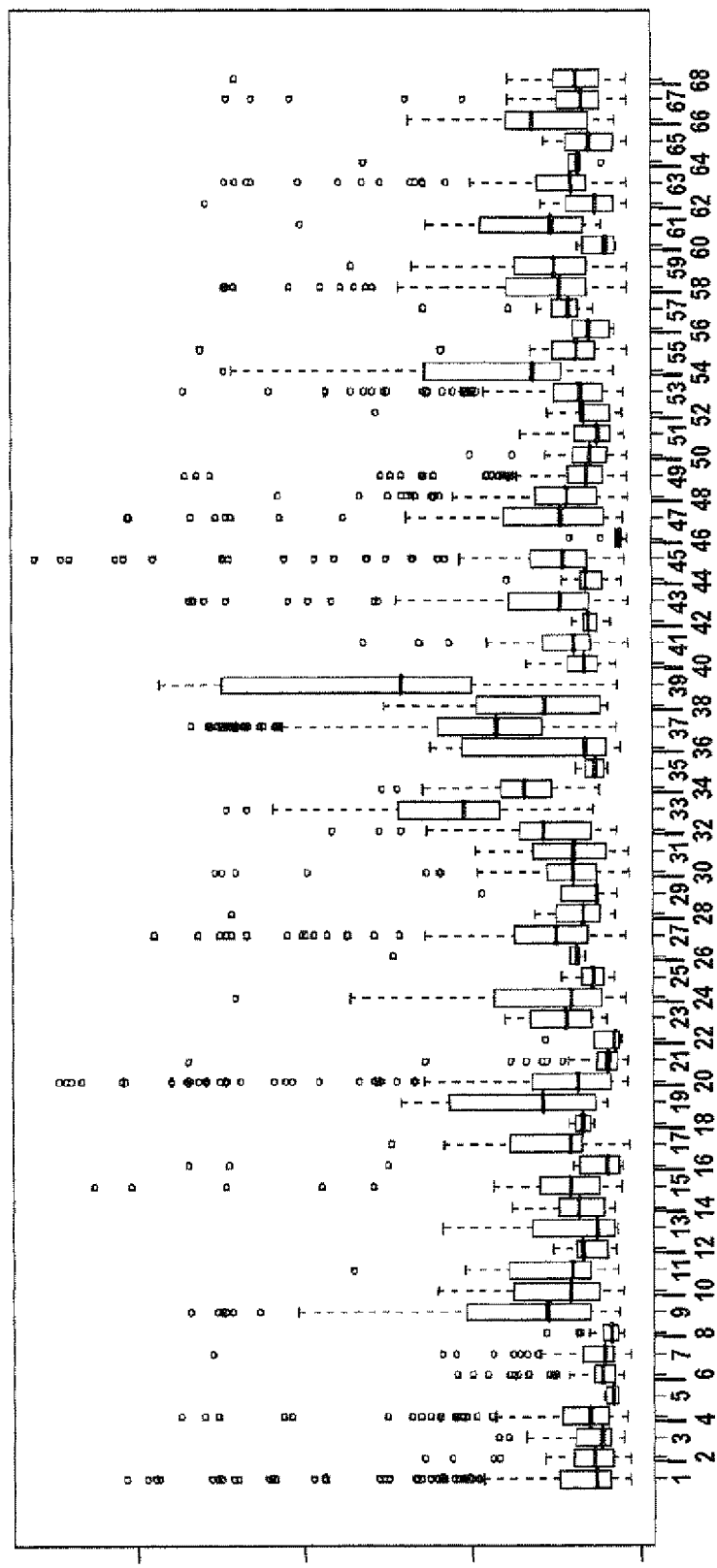
FIG. 12. Some patients of certain tumor types have aberrantly high levels of LIF. LIF mRNA levels in different tumor types showing that some patients (circles) have aberrantly high levels of LIF. Data obtained from GeneSapiens bioinformatics team (www.genesapiens.org). Numbers stand for: 1) pre-B cell acute lymphoblastic leukemia (B-ALL); 2) pre-T cell acute lymphoblastic leukemia (T-ALL); 3) B cell chronic lymphatic leukemia (B-CLL); 4) acute myeloid leukemia (AML); 5) Plasma cell leukemia; 6) Myeloma; 7) B-cell lymphoma; 8) Burkitts lymphoma; 9) T-cell lymphoma; 10) Chondrosarcoma; 11) Osteosarcoma; 12) Ewings sarcoma; 13) Synovial sarcoma; 14) Leiomyosarcoma; 15) Rhabdomyosarcoma; 16) Liposarcoma; 17) Sarcoma, not otherwise specified (NOS); 18) Skin, squamous cell carcinoma; 19) Melanoma; 20) Glioma; 21) Neuroblastoma; 22) Malignant Peripheral Nerve Sheath Tumors (MPNST); 23) Chordoma; 24) Oral squamous cell carcioma; 25) Laryngopharynx squamous cell carcioma; 26) Parotid gland, carcioma; 27) Lung adenocarcioma; 28) Lung, large cell cancer; 29) Lung, small cell cancer; 30) Lung, squamous cell carcioma; 31) Lung, carcinoid tumor; 32) Mesothelioma; 33) Esophagus adenocarcioma; 34) Gastric adenocarcioma; 35) gastrointestinal stroma tumors (GIST); 36) Small intestine, adenocarcioma; 37) Colorectal carcioma; 38) Liver cancer; 39) Pancreatic cancer; 40) Adrenal tumors; 41) Thyroid carcioma; 42) Renal oncocytoma; 43) Renal cancer; 44) Nephroblastoma; 45) Bladder cancer; 46) Testis, seminoma; 47) Testis, non-seminoma; 48) Prostate adenocarcioma; 49) Breast ductal cancer; 50) Breast lobular cancer; 51) Breast medullary cancer; 52) Breast cancer, others; 53) Breast carcioma, NOS; 54) Ovarian, clear cell carcioma; 55) Ovarian, endometrioid carcioma; 56) Ovarian, germ cell tumor; 57) Ovarian, mucinous carcioma; 58) Ovarian, serous carcioma; 59) Ovarian adenocarcioma, not otherwise specified (NOS); 60) Ovarian tumor, others; 61) Peritoneum adenocarcioma; 62) Uterine sarcoma; 63) Uterine adenocarcioma; 64) Uterine squamous cell carcioma; 65) Uterine, Mullerian tumor; 66) Cervical adenocarcioma; 67) Cervical squamous cell carcioma; 68) Vagina/Vulva carcinoma.

In another aspect, the invention relates to a prognostic in vitro method for predicting the average life expectancy of patients suffering from a disease associated with unwanted cell proliferation. This method is based on the observation that, e.g. in case of glioma, the average life expectancy is reduced for patients showing higher LIF expression levels than control patients (FIG. 12).

The method is based on
a) quantifying the expression levels of the IL-6 type cytokine in said patient, and
b) comparing said expression levels with control levels, wherein if the expression levels of an IL-6 type cytokine in said patient are greater than the values of control patients of that same disease, then said patient likely has a lower life expectancy than the control group.

In a more specific aspect, the concentration of the IL-6 type cytokine can be measured for prognostic purposes, namely for the prediction of average life expectancy of an individual suffering from said disease. For this purpose, the concentration of the IL-6 type cytokine of the tumor patient are compared to the reference concentration of that same IL-6 type cytokine. The group of reference patients typically consists of patients who are well documented and who suffer from the same disease. For example, the reference sample can be obtained from identical amounts of a group of at least 2, at least 10, at least 100 to more than 1000 individuals, such that the population of patients suffering from said disease is statistically significant. The reference group can consist of one or more of the following:
a) all patients suffering from said disease
b) all patients suffering from said disease who do not show significantly upregulated levels of the IL-6 type cytokine
c) all patients suffering from said disease who show significantly downregulated levels of the IL-6 type cytokine.

The concentration of IL-6 type cytokine can be determined intracellular, in the interstitial gap or in extracts in which both the intracellular protein and the one found in the interstitial gap. The levels of IL-6 cytokine can be determined by means of measuring the activity of said cytokine using assays suitable for that purpose, or by means of measuring the amount of protein using immunological methods or by means of measuring the mRNA corresponding to the IL-6 type cytokine.

In this aspect, a preferred embodiment is a disease associated with unwanted cell proliferation. In a more particular embodiment, the disease associated with unwanted cell proliferation is cancer. Even more preferred, the type of cancer is associated with abnormally high levels of the IL-6 type cytokine in a subset of patients of said cancer. In a more particular embodiment, the cancer is one of the following: leukemia, glioma, colorectal carcinoma, bladder cancer, breast cancer. In a more particular embodiment, the leukemia is pre-B cell acute lymphoblastic leukemia or acute myeloid leukemia and the breast cancer is breast ductal cancer or breast carcinoma.

The IL-6 type cytokines which can be used as markers for testing patients for prognostic purposes have been described with detail above and are selected from LIF, IL-6, IL-11, oncostatin M, cardiotrophin-1, CNTF and CLC.

Statistical methods will allow for predicting average life expectancy of patients based on the levels of the IL-6 type cytokine.

The invention is described below by means of the following examples which must be considered as merely illustrative and non-limiting examples thereof.

Example 1

1. Materials and Methods
1.1 Cell Lines and Primary Cell Cultures

The U373MG and A172 cells were a generous gift from J. Rich and D. Bigner and were cultured in DMEM with 10% fetal bovine serum (FBS). The primary culture of tumor cells (PCTC) and the GEM neurospheres were generated as described (Bruna et al., (2007) Cancer Cell 11, 147-160; Gunther et al., (2008) Oncogene. May 1; 27(20):2897-909). Briefly, the samples of tumors were processed in the 30 minutes after the surgical resection. The ground pieces of the samples of human gliomas were digested with 200 U/ml collagenase I (Sigma) and 500 U/ml of DNase I (Sigma) in PBS for 2 hours at 37° C. and with constant vigorous stirring. The suspension of individual cells was filtered through a 70 µm cell filter (BD Falcon) and washed with PBS. Finally, the cells were resuspended and subsequently cultured in DMEM with 10% FBS, for the culture of PCTCs, or in neurosphere medium in the case of the GBM neurospheres. The neurospheres of normal human neuroprogenitors were generated from human embryonic cerebral cortex tissue (12-16 weeks after the conception) collected after voluntary abortions. The samples were processed and cultured as described (Poltavtseva et al. (2002) Brain Res Dev Brain Res 134, 149-154). The neurosphere medium consists of neurobasal medium (Gibco) supplemented with B27 (Gibco), L-glutamine (Gibco), penicillin/streptomycin, and growth factors (20 ng/mL EGF and 20 ng/mL FGF-2 (Peprotech)).

The samples of human gliomas and human embryonic tissues were obtained from the Hospital Vall d'Hebron. The clinical protocol was approved by the Ethics Committee (CEIC) of Vall d'Hebron with the informed consent obtained from all the subjects.

1.2 Plasmids and Reagents

Genomic DNA of U373MG was used to amplify the −634/+32 region of the human LIF promoter which was cloned into the pGL2-basic luciferase vector. The deletion constructs (−267/+32), and (−73/+32) were generated by means of digestion of the construct (−634/+2). Two point mutations were introduced in positions −183 bp and −184 bp in the construct (−267/+32) to interrupt the Smad binding element (SBE) and generate the construct (−267/+32) mutSBE. TGFβ1, TGFβ2, TGFβ3 (R&D Systems), TβRI inhibitor (SB431542, Tocris), LIF (Chemicon), the neutralizing antibodies against LIF (R&D), JAK inhibitor (tetracyclic pyridone 6 (P6) Calbiochem), the assembly of SMART siRNAs targeted to Smad2, Smad3 and Smad4 (Dharmacon), and the control siRNA siGlo (Dharmacon) were used at the indicated concentrations. The antibodies specific against p-Smad2, Smad2, p-STAT3 (p-Tyr705) and total STAT3 (Cell Signalling) and against Smad2, Smad3 and Smad4 (Hata et al., (2000) Cell 100, 229-240) were used for Western blotting.

1.3 Immunocytochemistry, ELISA and Chromatin Immunoprecipitation

The immunocytochemistry of neurospheres and differentiated neurospheres was performed as described (Geshwind et al., 2001) using the following antibodies: anti-nestin (Chemicon), anti-GFAP (Dako), anti-TuJ1 (Chemicon), anti-O4 (Chemicon), anti-Sox2 (Chemicon), anti-α-tubulin (Sigma). The nuclei were counterstained with 4',6-diamino-2-phenylindole (DAPI).

For the quantitative determination of the levels of LIF protein secreted to the medium, the human LIF ELISA kit (R&D Systems) was used, following the manufacturer's specifications. The supernatant of U373MG cells or GEM neurospheres previously deprived of serum was collected after 48 hours of the indicated treatment. The floating cells were discarded and 5 mL of the supernatants were concentrated using Amicon Ultra-4 PLCC Ultracel-PL 5 kDa membranes (Millipore) to a final volume of 200 μl.

The chromatin immunoprecipitation was performed as described (Bruna et al., mentioned above). The series of proximal and distal primers of the LIF promoter cover the (−410/−165) and (−4534/−4293) regions, respectively.

1.4 Self-Renewal Assays

The self-renewal of the neurospheres was evaluated by seeding an identical number of cells at a very low density in wells of a 96-well plate. The cells were treated, in the absence of growth factors, with the indicated compounds and the total number of new neurospheres formed after 7 days in culture was counted (Lee et al. (2008) Cancer Cell 13, 69-80; Reynolds and Weiss, (1996) Dev Biol 175, 1-13; Seaberg and van der Kooy, (2002) J Neurosci 22, 1784-1793).

1.5 Quantitative Real-Time PCR qRT-PCR was performed using Taqman probes from Applied Biosystems, according to the manufacturer's recommendations. The reactions were carried out in a ABI 7000 sequence detector (Perkin Elmer) and the results were expressed as the fold change calculated by means of the DDCt method relative to the control sample or the first quantified sample. The ribosomal unit of 18S or β-actin were used as internal normalization controls.

1.6 Luciferase Assays

The A172 cells were transiently transfected with the different indicator constructs of the LIF promoter and plasmid pRL-TK of renilla luciferase (Promega) as a normalization control using Lipofectamine 2000 (Invitrogen).

1.7 Intracranial Tumor Assays

The indicated amounts of cells were stereotactically inoculated in the striate body of the right hemisphere of the brain (1 mm anterior, 1.8 mm lateral with respect to the bregma, and 3.0 mm intraparenchymal) of seven week old Balbc nu/nu female mice (Charles River Laboratories). The mice were sacrificed when they presented neural symptoms or a significant weight loss. Studies were conducted by magnetic resonance imaging (MRI) in a 9.4T vertical magnet in an interface with a AVANCE 400 system (Bruker). Under anaesthesia with xylazine/ketamine, the mice were given an intravenous injection of an MRI contrast agent, gadolinium diethylenetriamine pentaacetic acid, at a dose of 0.25 mmol Gd/kg of weight and were placed in a 18 radio frequency coil (internal diameter, 35 mm). After the localizer took images on three orthogonal axes, the images of the entire brain of the mouse were acquired.

1.8 Statistical Analyses

A Spearman's correlation test was used to analyze the relationships between LIF and TGFβ2, Musashi-1, Sox2 and Nestin. The data in the graphs are presented as the mean±s.d.

Example 1

TGFβ Induces the Self-Renewal of GICs Derived from Patient

Figure 2:
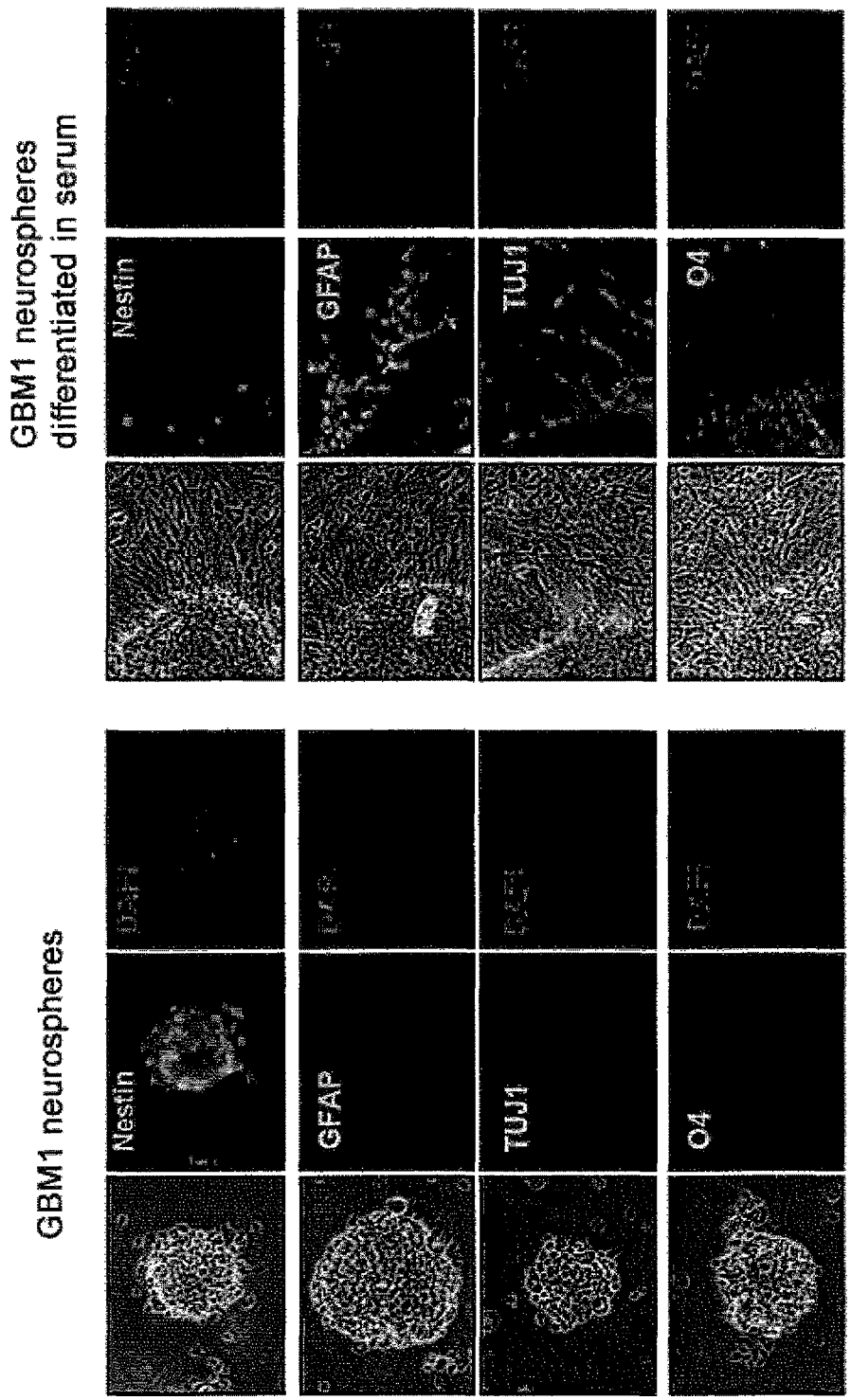
FIG. 2. Immunocytochemistry of the indicated markers in neurospheres derived from GBM1, and neurospheres differentiated in serum derived from GBM1.

To study the effect of TGFβ on the capacity for self-renewal of GICs (glioma initiating cells), cells were obtained from samples of surgically removed human GBMs (glioblastoma multiforme). From the same sample of tumor, on one hand primary cultures of tumor cells (PCTCs) were generated in the presence of serum and, in parallel, tumor cells were cultured in serum-free medium in the presence of EGF and FGF. The cells cultured in serum-free medium supplemented with EGF and FGF quickly generated non-adherent multicellular spheres (neurospheres) as has been described (Galli et al., (2004) Cancer Res 64, 7011-7021; Gunther et al., mentioned above; Lee et al., (2006) Cancer Cell 9, 391-403; Singh et al. (2003) Cancer Res 63, 5821-5828) (FIG. 1A). The neurospheres generated from the samples of tumor expressed high levels of the neuroprogenitor cell markers Musashi-1, Sox2 and Nestin (FIG. 1B), and experienced multilineage differentiation acquiring the expression of GFAP (astrocyte marker), Tuj-1 (neuronal marker), and O4 (oligodendrocyte marker) when they were cultured in the presence of serum (FIG. 2). Furthermore, the neurospheres derived from tumors were very oncogenic compared to the PCTCs. The cells of the neurospheres and the PCTCs were orthotopically implanted in the brain of immunosuppressed mice. The tumor growth was evaluated by means of magnetic resonance imaging (MRI) and the weight of the mice was monitored. The cells of the neurospheres generated tumors 30-60 days after the inoculation, which caused an intense weight loss, while the PCTCs did not grow in tumors during the same time interval in all the cases (FIG. 1C). Thus, the neurospheres generated from samples of human GBMs expressed neuroprogenitor cell markers, showed multilineage differentiation potential, and were very oncogenic. All these characteristics indicated that the neurospheres obtained from GBMs derived from patients were enriched in GICs.

It was decided to evaluate the effect of TGFβ on the capacity for self-renewal of GICs following a well described protocol based on the capacity of GICs to generate neurospheres (Reynolds and Weiss, 1996, Dev Biol. 175:1-13; Seaberg and van der Kooy, 2002, J Neurosci 22:1784-1793). The neurospheres derived from patients were disassociated into individual cells, treated with TGFβ or left untreated for 7 days in the absence of growth factors and the newly formed neurospheres and the total number of cells were counted. Following this protocol, the effect of TGFβ on the capacity for self-renewal of the GICs derived from three different patients was evaluated. The treatment with TGFβ significantly increased the number of neurospheres and increased the total number of cells (FIG. 1D, 1E, 1F). These effects were blocked when an TGFβ I receptor inhibitor (TβRI) was added at the same time as TGFβ. The isolated TβRI inhibitor had no significant effect (FIG. 1D, 1E, 1F). These results showed that the TGFβ pathway increased the self-renewal of GICs.

Example 2

TGFβ Induces the Expression of LIF in Cells of Human GBM

It was decided to investigate the molecular mechanisms responsible for the effect of TGFβ on GICs. Gene responses to TGFβ in GBM cells which could be involved in the regulation of the self-renewal of GICs were investigated. In a previous work (Bruna et al., 2007), transcriptome analyses were conducted in the U373MG glioma cell line treated with TGFβ and/or a TβRI inhibitor. LIF was among the 63 gene responses to TGFβ in U373MG which were dependent on the activity of TβRI. The LIF-LIFR/gp130-JAK-STAT signaling pathway has been implicated in the self-renewal of stem cells, both in embryonic stem cells (Niwa et al., 1998, Genes Dev, 12: 2048-2060; Williams et al., 1988, Nature, 336:684-687) and in neuroprogenitor cells (Bauer and Paterson, 2006, J Neurosci, 26:12089-12099; Molne et al., 2000, J Neurosci Res, 59:301-311; Wright et al., 2003, J.

Figure 3:
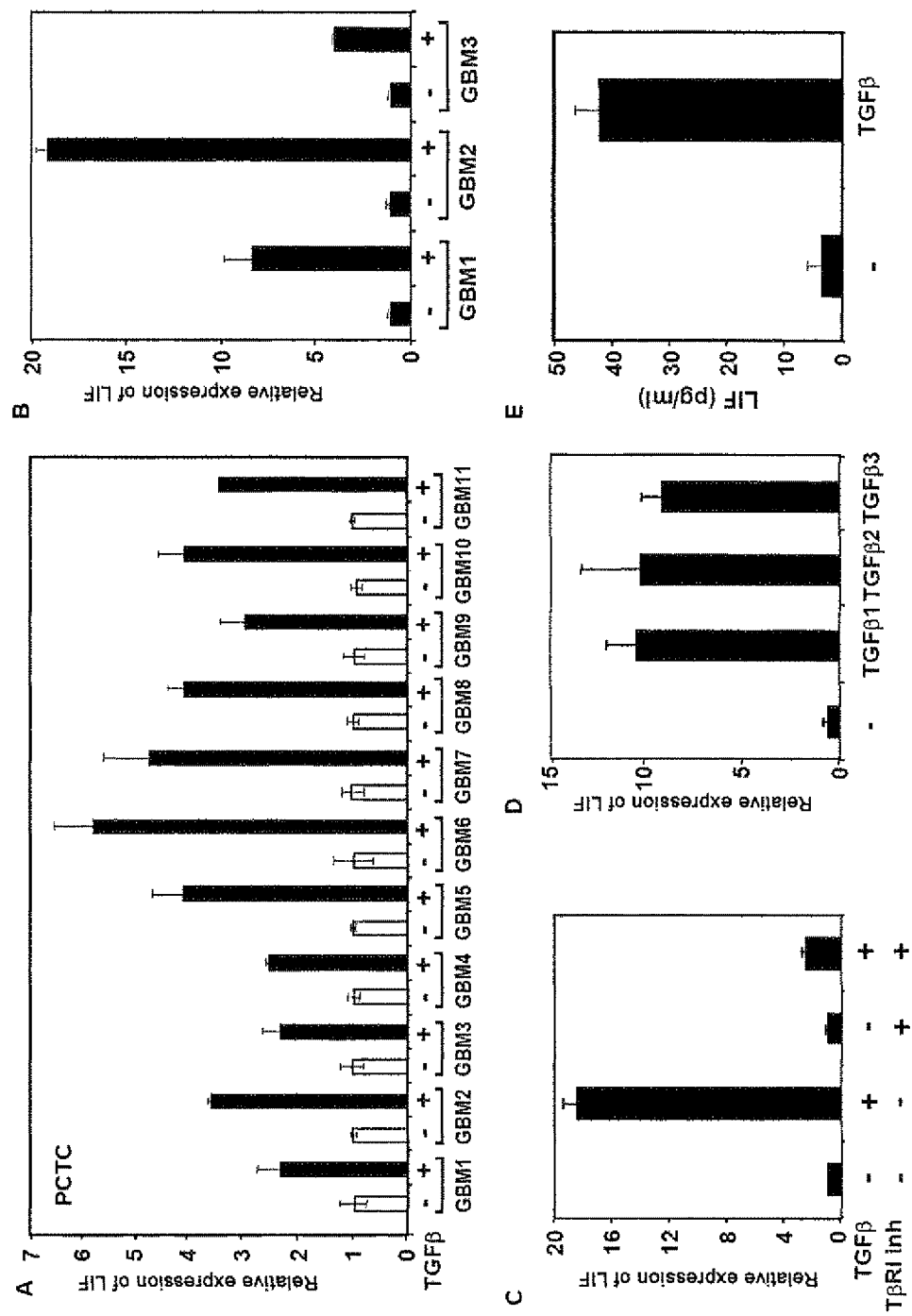
FIG. 3. TGFβ induces the expression of LIF in PCTC and GBM neurospheres. (A) PCTC cells of the 11 samples of the indicated GBM (GBM1-11) were treated with 100 pM TGFβ1 for 3 hours in medium without serum or left untreated, and the expression levels of LIF were determined by means of qRT-PCR. The β-actin was determined as an internal normalization control. (B) GBM neurosphere cells were treated as in A and the expression levels of LIF were determined by means of qRT-PCR as in A. (C) GBM neurospheres were incubated with 100 pM TGFβ1 and/or 2 µM TβRI inhibitor for 3 hours in medium without serum and the mRNA levels of LIF were determined by means of qRT-PCR as in A. (D) GEM1 neurospheres were incubated with 100 pM TGFβ1, TGFβ2 and TGFβ3 for 3 hours in medium without serum and the mRNA levels of LIF were determined by means of qRT-PCR as in A. (E) The levels of LIF protein secreted were determined by means of ELISA in GBM1 neurospheres after 48 hours of treatment with 100 pM TGFβ1.

Neurochem, 86:179-195) and it was hypothesized that LIF could mediate the effect of TGFβ on GICs. It was first determined if the induction of the LIF transcript mediated by TGFβ was observed in tumor cells derived from patients. A panel of PCTCs derived from 11 different human GBMs was treated with TGFβ for 3 hours and the levels of LIF mRNA were determined. TGFβ induced LIF in all the PCTCs assayed (FIG. 3A). These results indicated that the induction of LIF by TGFβ is a common phenomenon which takes place in most human GBMs. Furthermore, TGFβ was capable of inducing the LIF transcript in neurospheres derived from patients (FIG. 3B) and this effect was dependent on the activity of TβRI since the induction of LIF by TGFβ was blocked in the presence of a TβRI inhibitor (FIG. 3C). Three members of the TGFβ family (TGFβ1, TGFβ2, and TGFβ3) were capable of inducing LIF in neurospheres derived from patients (FIG. 3D) and, as expected, the induction of the LIF transcript by TGFβ resulted in an increase in the secretion of the LIF protein when it was measured by means of ELISA in conditioned neurosphere medium (FIG. 3E).

Example 3

Figure 4:
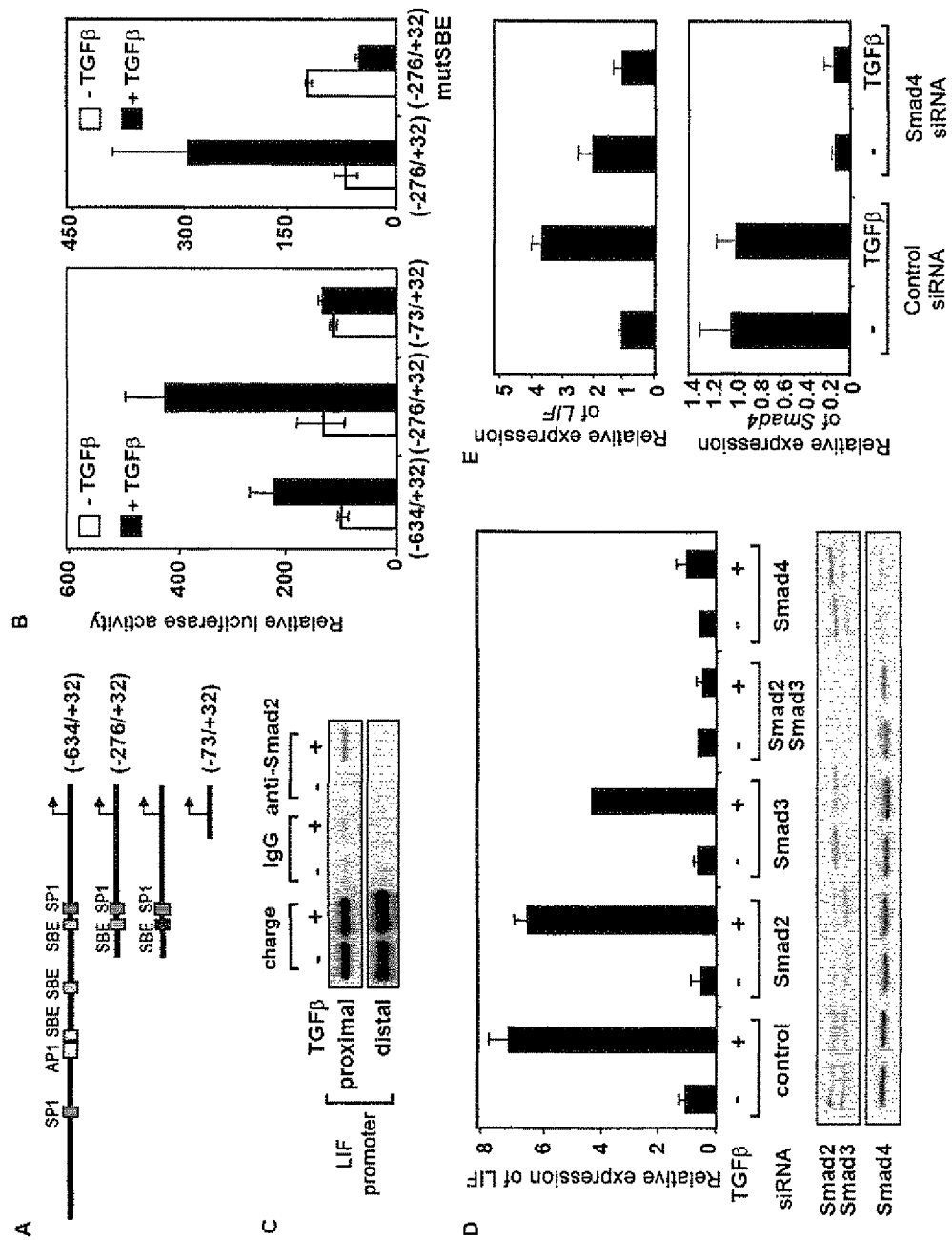
FIG. 4. TGFβ induces the transcription of LIF through an activated Smad complex. (A) Diagrams of the indicator constructs of luciferase LIF. (B) A172 glioma cells were transfected with indicator constructs of luciferase LIF (−634/+32), (−276/+32), (−276/+32) mutSBE or (−73/+32). 16 hours after transfection, the cells were treated with 100 pM TGFβ1 for 20 hours and were analyzed for luciferase activity. (C) U373MG cells were treated with 100 pM TGFβ1 for 3 hours, and ChIP assays were performed with the indicated antibodies and the PCR primers indicated. (0, E) The levels of LIF were determined by means of qRT-PCR analysis in U373MG (D) or GEM neurospheres (E) treated with 100 pM TGFβ1 for 3 hours after silencing mediated by siRNA of the indicated members of the indicated Smad family. Western blotting was performed using antibodies specific for Smads or qRT-PCR of Smad4. The β-actin was determined as an internal normalization control.

TGFβ Induces the Expression of LIF Through an Activated Smad Complex which Binds to the LIF Promoter To study the transcriptional regulation of LIF by TGFβ, the human LIF promoter was cloned in a pGL2-basic reporter construct. TGFβ was capable of transactivating the reporter constructs which contained the −634/+32 and −276/+32 regions of the LIF promoter in U373MG cells. The −73/+32 fragment of the LIF promoter lost the transcriptional response to TGFβ, indicating that the element of response to TGFβ was included in the −276/−73 region (FIG. 4A, 4B). This region contains a single Smad binding element (SEE, 5'GTCT-3') close to a SP1 binding site (FIG. 4A). The SBE was mutated and it was observed that the response to TGFβ was eliminated (FIG. 45), indicating that an activated Smad complex binds to the proximal SEE in the LIF promoter to induce transcription. Chromatin immunoprecipitation (ChIP) assays were performed and it was observed that endogenous Smad2 bound to the proximal region of the LIF promoter and not to the distal region 4 kb upstream from the transcription initiation site in cell treated with TGFβ (FIG. 4C). To finally show that the Smads are involved in the induction of the expression of LIF by TGFβ, Smad2, Smad3, both Smad2 and 3, and Smad4 were silenced using interfering RNA. The induction of LIF by TGFβ decreased when Smad2 and Smad3, or Smad4 were decreased, indicating that an activated Smad complex is required for the transcriptional response of LIF to TGFβ (FIG. 4D). Smad2 and Smad3 are redundant in this process since the silencing of each Smad separately did not significantly affect the levels of LIF induced by TGFβ (FIG. 4D). As expected, the induction of LIF by TGFβ in neurospheres derived from patients also depended on Smad. The silencing of Smad4 in human GEM canceled the response of LIF to TGFβ (FIG. 4E).

Example 4

Figure 5:
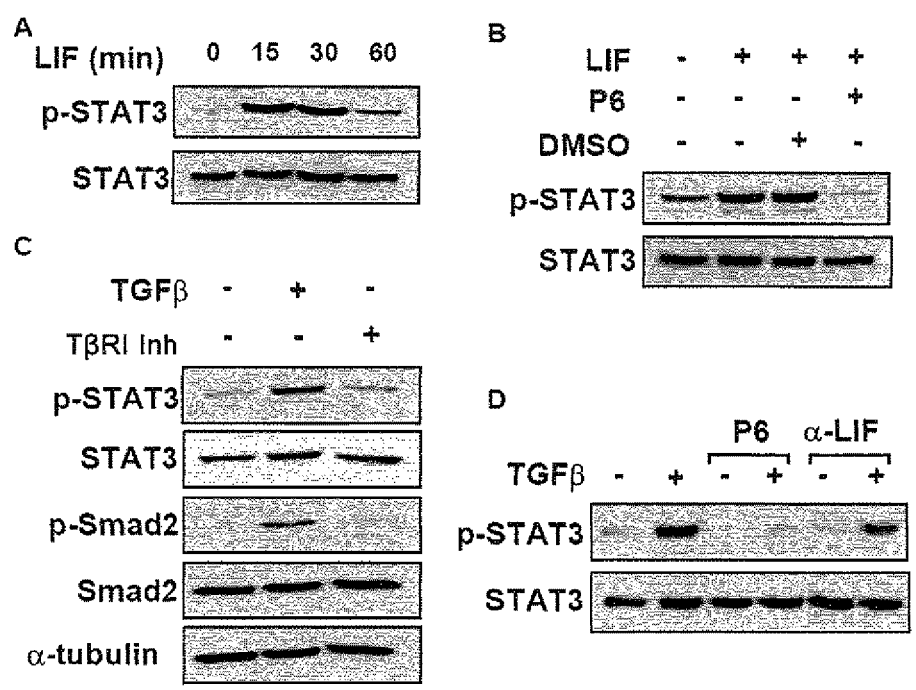
FIG. 5. TGFβ induces the LIF-JAK-STAT pathway in GEM neurospheres derived from patients. (A) The levels of p-STAT3 and STAT3 were determined by means of Western blotting of neurospheres of the sample of GBM1 treated with 20 ng/ml LIF for the indicated time periods. (B) The neurospheres of the sample of GBM1 were treated with 20 ng/ml LIF and/or 0.5 µM P6 for 15 minutes and the levels of total p-STAT3 and STAT3 were determined by means of Western blotting. (C) The neurospheres of the sample of GBM1 were treated with 100 pM TGFβ1 or the 2 µM TβRI inhibitor for 4 hours in the absence of EFG and FGF and the levels of p-STAT3, STAT3, p-Smad2, Smad2 and α-tubulin were determined by means of Western blotting. (D) the neurospheres of the sample of GBM1 were treated with 100 pM TGFβ1, 0.5 µM P6 or the blocking antibody against LIF for 4 hours in the absence of EGF and FGF and the levels of total p-STAT3 and STATS were determined by means of Western blotting.

TGFβ Induces the JK-STAT Pathway Through the Induction of LIF in Neurospheres Derived from Patients In order to distinguish whether the LIF signaling pathway is functional in GEM neurospheres, the neurospheres were treated with recombinant LIF and the levels of phosphorylation of the downstream substrate of the LIF receptor complex, STAT3, were determined. Recombinant LIF induced a quick phosphorylation of STAT3, indicating that the neurospheres derived from patients expressed a functional LIF receptor complex (FIG. 5A). Furthermore, the induction of p-STAT3 was prevented by the presence of a pharmacological JAK-specific, tetracyclic pyridone 6 (P6) (Pedranzini et al., 2006, Cancer Res, 66: 9714-9721; Thompson et al., 2002, Bioorg Med Chem Lett, 12:1219-1223) (FIG. 5B). Interestingly, TGFβ induced the phosphorylation of STAT3 in GEM neurospheres and the TβRI inhibitor prevented that effect (FIG. 5C). It was decided to assess whether LIF was mediating the induction of p-STAT3 by TGFβ. For this purpose, a neutralizing antibody against LIF was used to specifically block the effect of secreted LIF on cells treated with TGFβ. The presence of the neutralizing antibody of LIF decreased the induction of p-STAT3 by TGFβ. Furthermore, the levels of p-STAT3 in cells treated with TGFβ were repressed by means of the treatment with P6 (FIG. 5D). These results indicated that TGFβ was capable of activating the JAK-STAT pathway in neurospheres derived from patients through the induction of the secretion of LIF which acted by means of a autocrine/paracrine loop.

Example 5

LIF Mediates the Induction of the Self-Renewal of GICs by TGFβ

Figure 6:
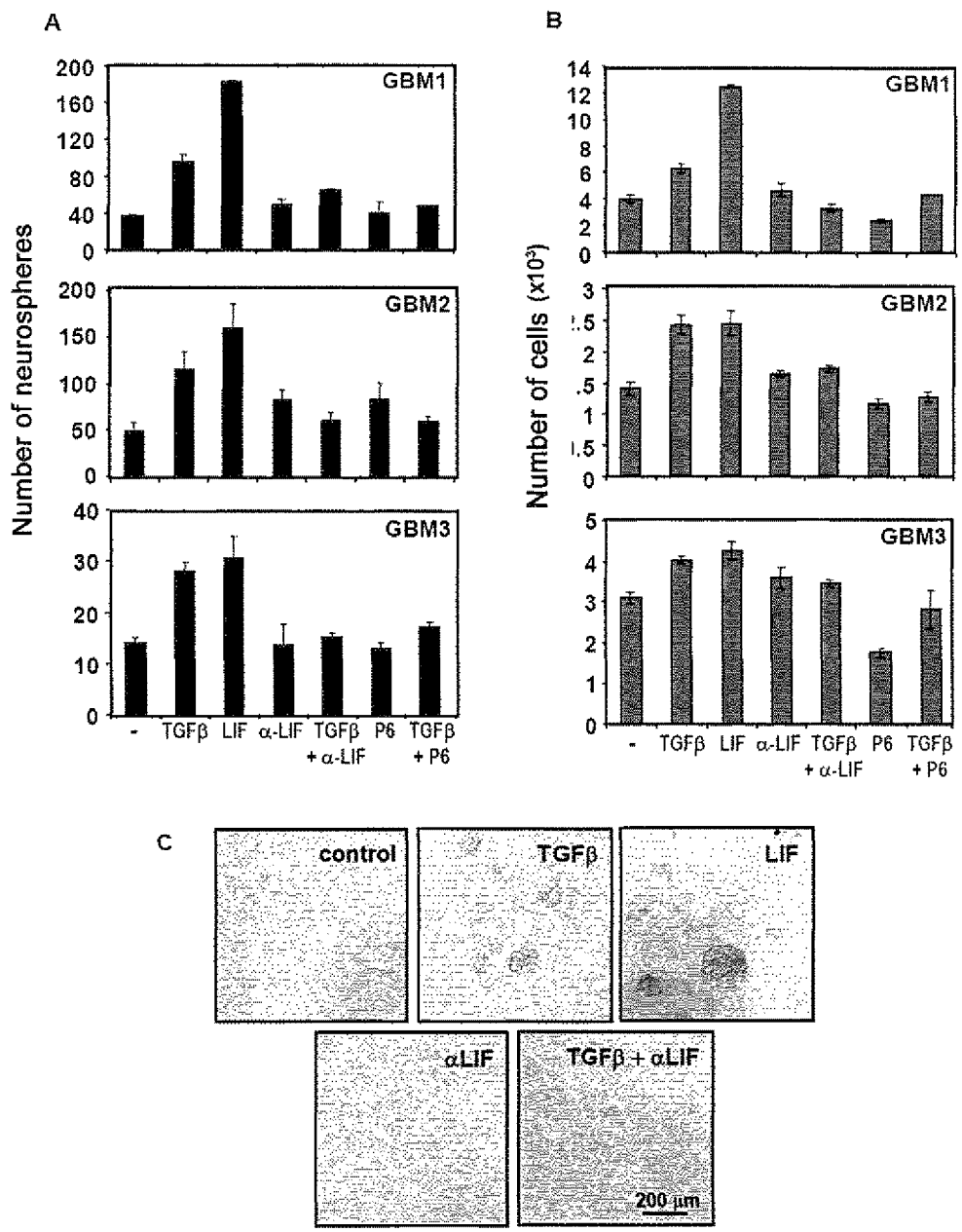
FIG. 6. LIF mediates the increase of self-renewal of GIC by TGFβ. (A, B) GBM1, GBM2 and GBM3 neurosphere cells were treated with 100 pM TGFβ1, 20 ng/ml LIF and/or anti-LIF neutralizing antibody and 0.5 µM P6 in the absence of EGF and FGF and the number of newly formed neurospheres (A) or the total number of cells (B) was determined. (C) Representative images of GBM1 neurospheres treated as indicated in A and B.

It was decided to assess whether LIF and JAK-STAT pathway mediated the increase of self-renewal of GICs by TGFβ. For this purpose, the neutralizing antibody against LIF and P6 was used to specifically block the effect of the secreted LIF on cells treated with TGFβ. The neurospheres were disassociated into individual cells and were treated with TGFβ, recombinant LIF, anti-LIF antibody and/or P6. The newly formed neurospheres and the total number of cells were counted. Recombinant LIF increased the amount of newly formed neurospheres as well as the total number of cells, indicating that LIF induces the self-renewal of GICs (FIG. 6A, 6B, 6C). The treatment with the neutralizing antibody of LIF decreased the induction of the self-renewal of GICs by TGFβ. Furthermore, P6 repressed the effect of TGFβ on the self-renewal of GICs, indicating that the effect of the TGFβ on the self-renewal was dependent on the activity of JAK (FIG. 6A, 6B, 6C). As a whole, these data showed that TGFβ induced the capacity of self-renewal of GICs derived from patients through the LIF-JAK-STAT pathway.

Example 6

TGFβ Prevents the Differentiation of GICs Through LIF

Figure 7:
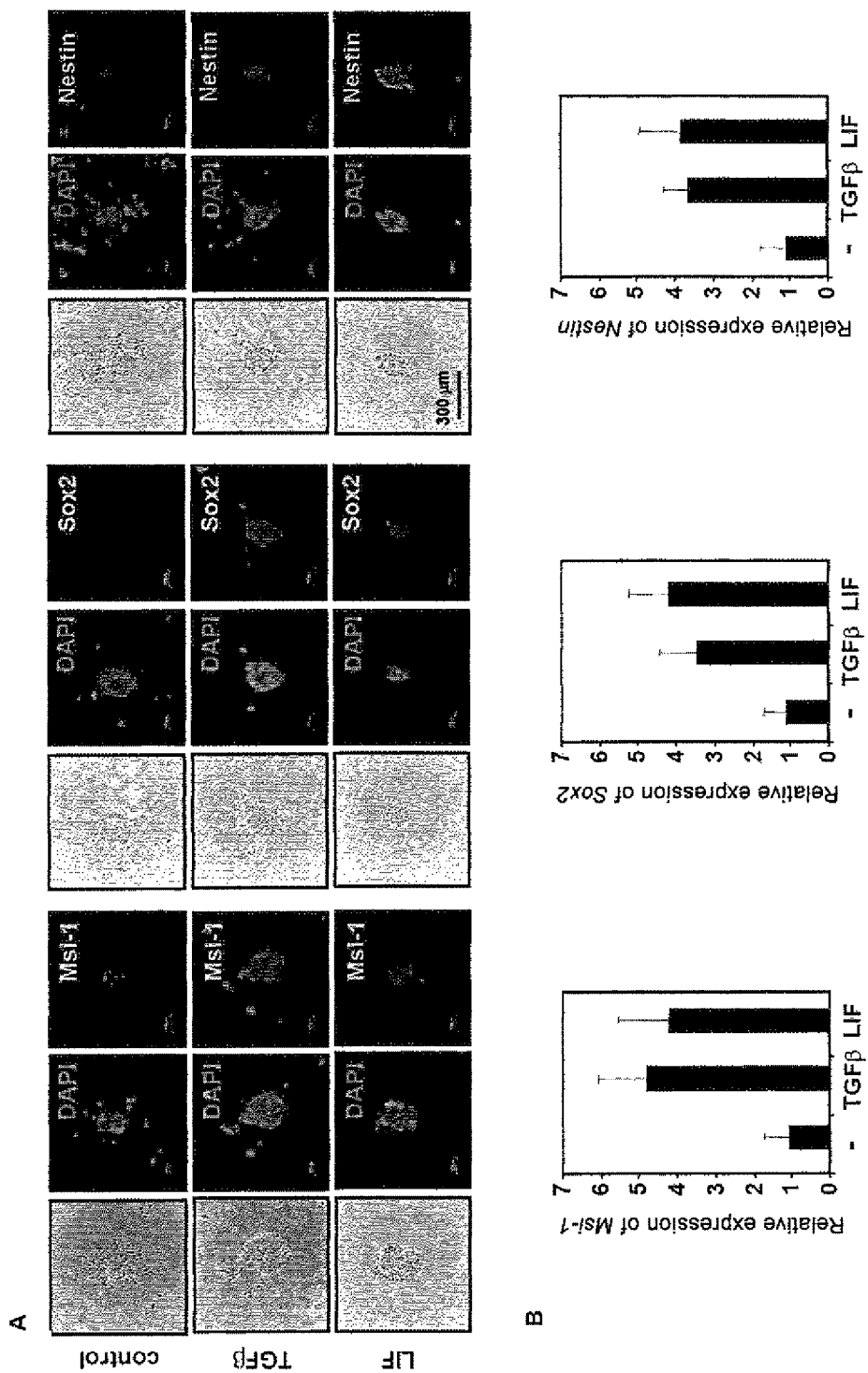
FIG. 7. TGFβ and LIF prevent the differentiation of GBM neurospheres. (A) Immunocytochemistry of the indicated proteins was performed in neurospheres derived from GBM1 treated with 100 pM TGFβ1 or 20 ng/ml LIF for 7 days in the absence of growth factors and the last 3 days on slides coated with poly-L-lysine. (B) The mRNA levels of Musashi-1 (Msi-1), Sox2 and Nestin were determined in GBM1 neurospheres after 7 days of the indicated treatments without growth factors. The RNA levels of 18S were used as an internal normalization control.

The neurospheres derived from GBMs grown in the absence of growth factors and seeded in poly-L-lysine-coated plates tend to differentiate losing the expression of the neuroprogenitor markers Musashi-1, Sox2 and Nestin, and being adhered to the culture plate. It was decided to evaluate the effect of TGFβ and LIF on this differentiation process. The neurospheres were cultured in the presence of TGFβ or LIF without EGF or FGF for 7 days and subsequently processed for immunohistochemical staining and qRT-PCR assays for determining the levels of the neuroprogenitor markers Musashi-1, Sox2 and Nestin. The neurospheres treated with TGFβ or LIF differed morphologically from the control cells in that they adhered less to the culture plate, maintaining the spherical structure. Furthermore, the cells treated with TGFβ or LIF maintained the expression of Musashi-1, Sox2 and Nestin detected by means of immunocytochemical assays (FIG. 7A) and quantified by means of qRT-PCR (FIG. 7B). This indicated that TGFβ and LIF are factors which not only regulate the self-renewal of GICs but are also involved in preventing the differentiation of GICs.

Example 7

Effect of TGFβ and LIF on Normal Human Neuroprogenitors

Figure 8:
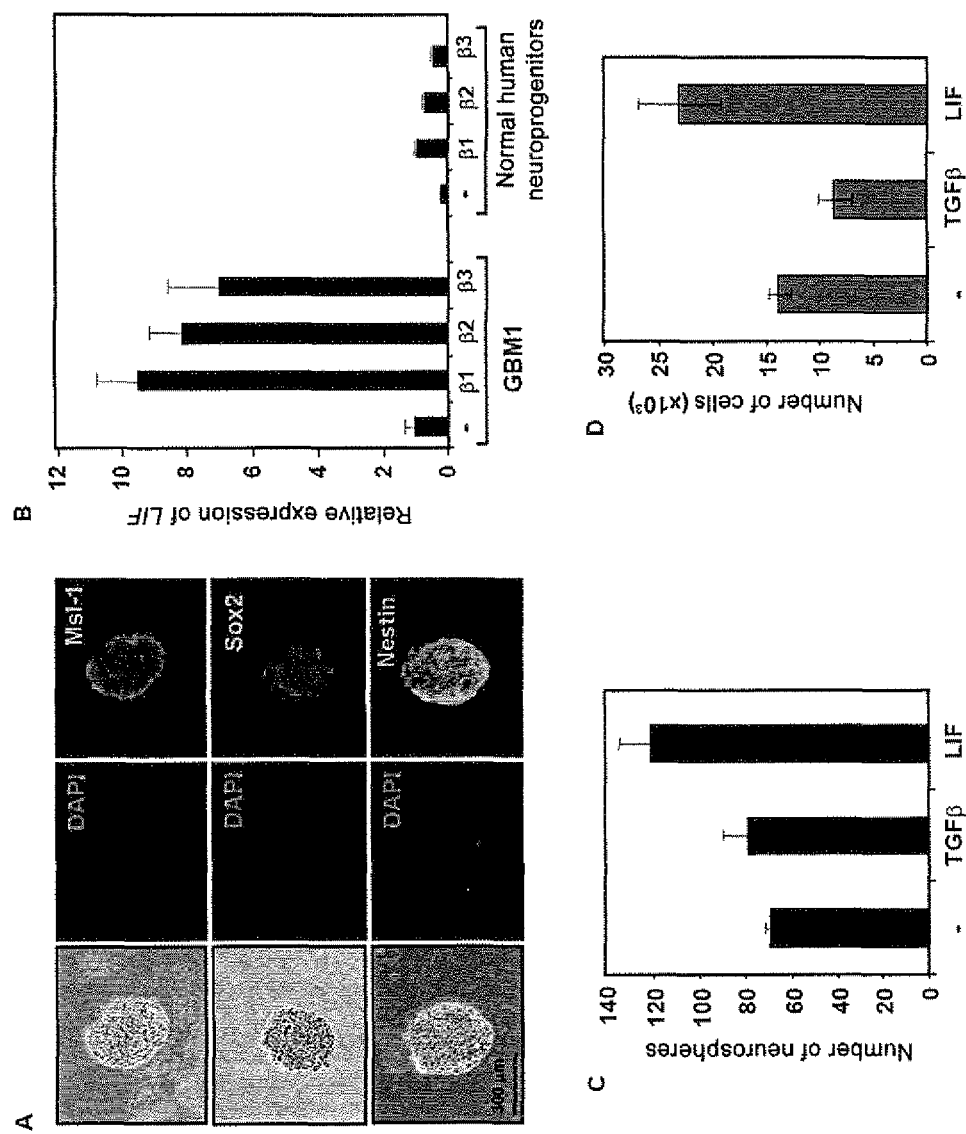
FIG. 8. Effect of TGFβ on the capacity of self-renewal of normal human neuroprogenitors. (A) Immunocytochemistry of the indicated markers was performed in human neuroprogenitor neurospheres. (B) Neurospheres of the sample of GBM1 and of human neuroprogenitors were incubated with the indicated members of the 100 pM TGFβ family for 3 hours and the mRNA levels of LIF were determined. (C, D) Neurosphere cells of normal human neuroprogenitors were incubated in the same conditions that have been described above in FIG. 1D in the presence of 100 pM TGFβ1 or 20 ng/ml LIF for 7 days and the number of newly formed neurospheres (C) and the number total of cells (D) were determined.

These data indicated that TGFβ and LIF were regulating the self-renewal and differentiation of GICs. It was decided to assess whether this effect was specific to tumor cells or was also present in normal neuroprogenitor cells. To answer this question, neuroprogenitor cells were obtained from samples of human fetal cerebral cortex (from 12 to 16 weeks after conception). As has been previously described (Carpenter at al., 1999, Exp Neurol, 158: 265-278; Poltavtseva at al., 2002, Brain Res Dev Brain Res, 134: 149-154; Wright at al., 2003, J Neurochem, 86: 179-195), human neuroprogenitors generated neurospheres when they were grown in serum-free medium supplemented with EGF and FGF and these neurospheres expressed Musashi-1, Sox2 and Nestin similarly to GBM neurospheres (FIG. 8A). First, it was determined if TGFβ induced LIF in normal human neuroprogenitors. Normal neurospheres did not induce LIF in response to TGFβ1, TGFβ2 or TGFβ3 compared with GEM neurospheres (FIG. 8B). Furthermore, TGFβ did not induce LIF in mouse neuroprogenitors obtained from mouse embryos or from the subventricular area of adult mice (data not shown). This indicated that the induction of LIF by TGFβ is specific to GBM neurospheres. As expected, since TGFβ did not induce LIF, TGFβ did not increase the capacity for self-renewal of normal neuroprogenitors and the number and size of the neuroprogenitor neurospheres did not increase by the treatment with TGFβ. In fact, the neurospheres treated with TGFβ were smaller and the total number of cells had decreased due to the presence of TGFβ (FIG. 8C, 8D). On the other hand, LIF increased the number and size of the newly formed neurospheres as well as the total number of cells (FIG. 8C, 8D) according to previous articles (Bauer and Patterson, 2006; Wright at al., 2003). Thus, LIF has the same effect on the self-renewal in GBM and normal neurospheres. On the contrary, there is a difference in the effect of TGFβ on the capacity for self-renewal of normal and tumor neurospheres due to the incapacity of TGFβ to induce LIF normal in neuroprogenitors.

Example 8

Figure 9:
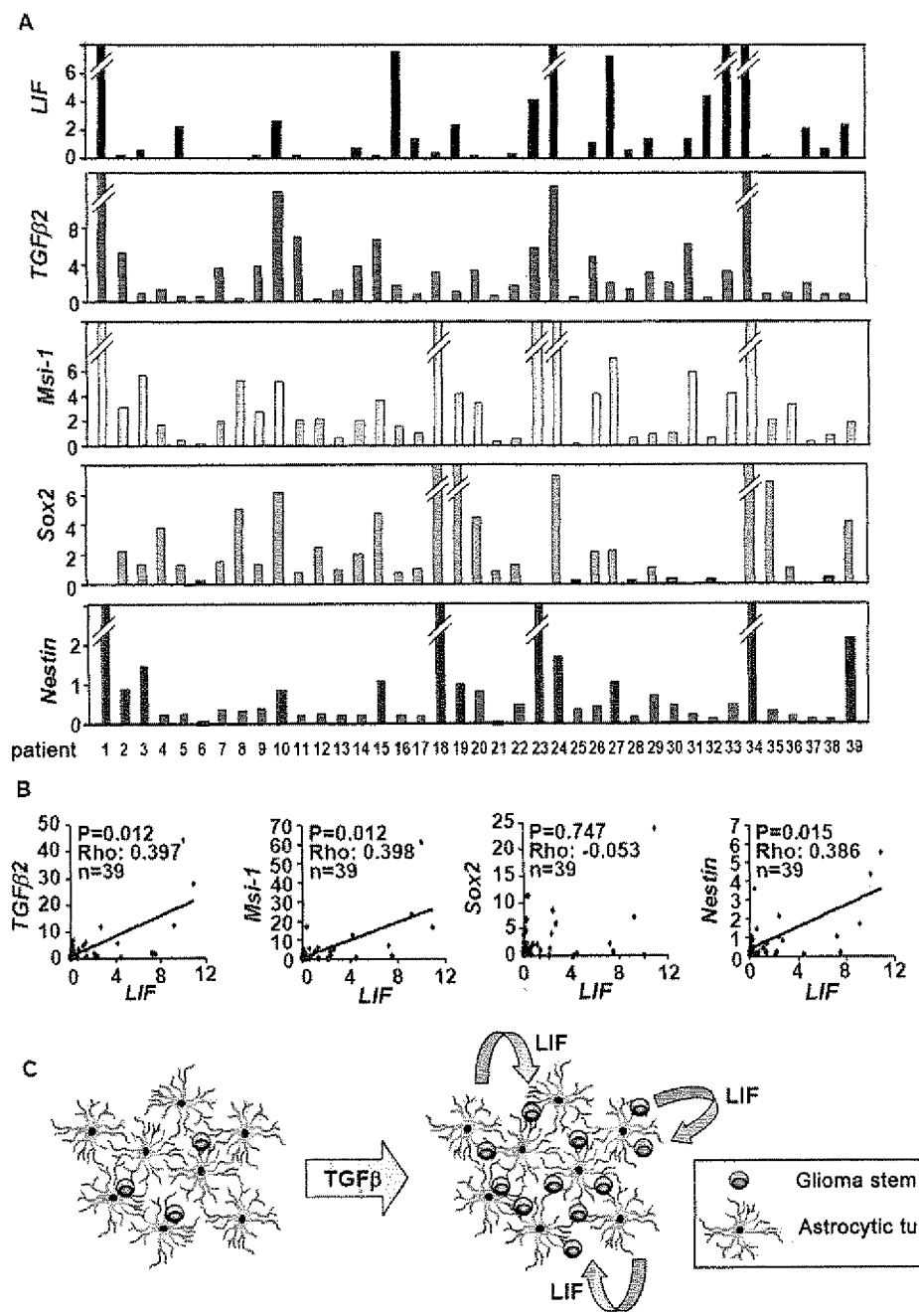
FIG. 9. Expression of LIF in human glioma tumors. (A) those of the LIF, TGFβ2, Musashi-1 (Msi-1), Sox2 and Nestin transcripts were determined by means of qRT-PCR analysis in 39 samples derived from human glioma patients. (B) Correlations between LIF and TGFβ2, Musashi-1 (Msi-1), Sox2 or Nestin. Spearman's rank correlation coefficient (Rho), two-tailed significance. (C) TGFβ foments the self-renewal of GSC by means of the induction of LIF increasing the amount of the group of stem cell-like cells within the tumor mass FIG. 10. LIF mRNA levels of glioma patients are linked to average life expectancy. Kaplan-Meier curves showing that the overall survival of glioma patients with LIF mRNA levels upregulated ≥2 fold is significantly lower than the rest of the patients (p=7.2E-8) by log-rank test. Data obtained from REpository for Molecular BRAin Neoplasia DaTa (REMBRANDT) program form the National Cancer Institute.

The Expression of LIF in Human Gliomas is Correlated with TGFβ2 and Neuroprogenitor Markers To evaluate if LIF was expressed in human gliomas, the levels of LIF in a panel of 39 gliomas were analyzed. It was observed that LIF was expressed in 17 and were highly expressed in 4-6 of the 39 gliomas (FIG. 9A), indicating that a large proportion of human gliomas expressed LIF. Since LIF is induced by TGFβ and it was found in previous works that TGFβ2 is responsible for the high TGFβ activity observed in gliomas (Bruna et al., 2007, mentioned above), it was evaluated if the TGFβ2 was involved in the expression of LIF. Indeed, the levels of LIF were correlated with TGFβ2 in the panel of gliomas, additionally supporting the fact that TGFβ2 is responsible for the induction of LIF in human gliomas (FIG. 9A, B). If LIF promotes the self-renewal of GICs, the group of this type of cells should be enriched in tumors which express high levels of LIF. To test this hypothesis, the levels of LIF were compared with the expression of GIC/neuroprogenitor markers. The levels of LIF correlated with the expression of Musashi-1 and Nestin but not of Sox2 (FIG. 9A, B), indicating that LIF foments the self-renewal of GIC and increases the group of GICs present in the tumor mass.

Example 9

Patients with Glioma or Glioblastoma have a Shorter Overall Life Expectancy

Figure 10:
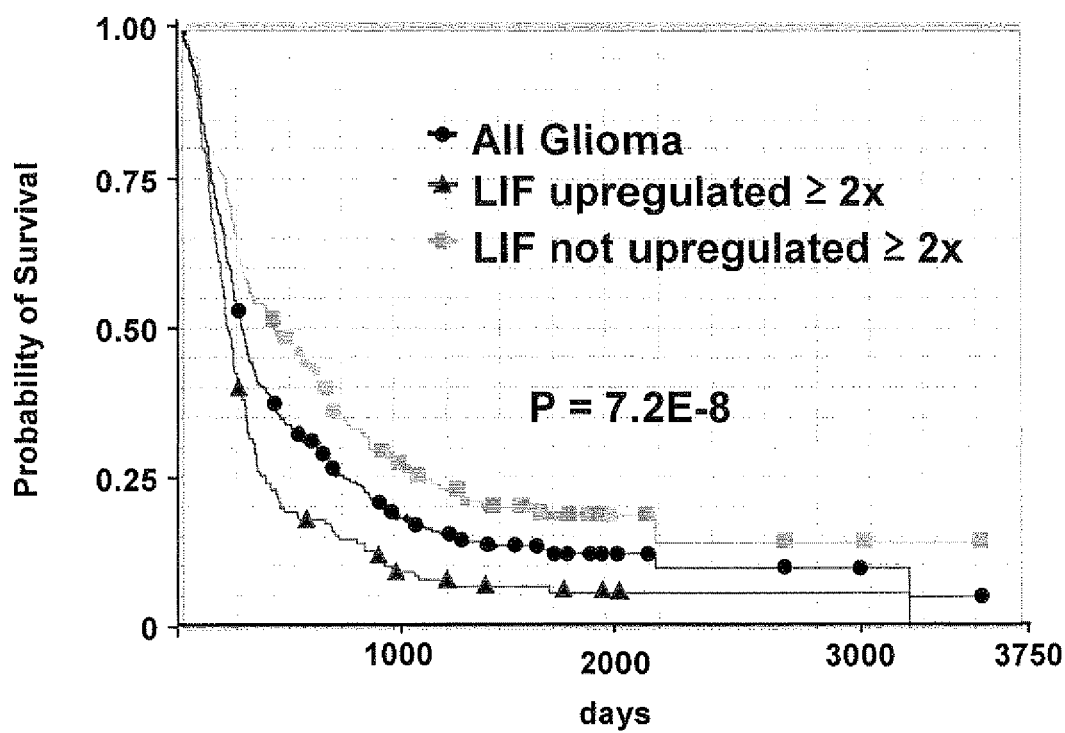

In a subset of all glioma patients, LIF levels are upregulated ≥2 fold. Over a set period of time, those patients have a significantly reduced probability of survival compared to control patients. For example, the probability of survival after 1000 days is reduced to approximately 50% compared with all glioma patients, and to approximately 35% compared to glioma patients with LIF levels not upregulated ≥2 fold (FIG. 10). Data obtained from REpository for Molecular BRAin Neoplasia DaTa (REMBRANDT) program form the National Cancer Institute.

Figure 11:
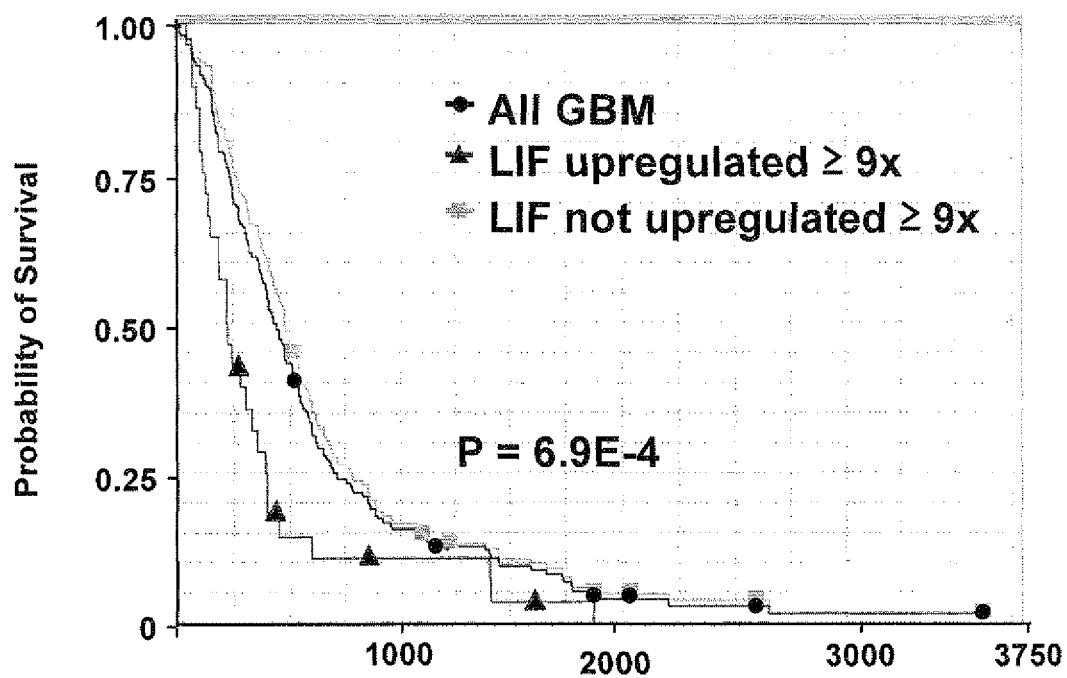
FIG. 11. LIF mRNA levels of glioblastoma (GEM) patients are linked to average life expectancy. Kaplan-Meier curves showing that the overall survival of GEM patients with LIF mRNA levels upregulated ≥9 fold is significantly lower than the rest of the patients (p=6.9E-4) by log-rank test. Data obtained from REpository for Molecular BRAin Neoplasia DaTa (REMBRANDT) program form the National Cancer Institute.

In a subset of all glioblastoma patients, LIF levels are upregulated ≥9 fold. Over a set period of time, those patients have a significantly reduced probability of survival compared to control patients. For example, the probability of survival after 500 days is reduced to approximately 50 compared with all glioblastoma patients (FIG. 11). Data obtained from REpository for Molecular BRAin Neoplasia DaTa (REMBRANDT) program form the National Cancer Institute.

Example 10

LIF mRNA Levels are Abnormally High in Diverse Types of Tumors

Some patients of certain tumor types have aberrantly high levels of LIF, as indicated by aberrantly high levels of LIF mRNA (FIG. 12). Data obtained from GeneSapiens bioinformatics team (www.genesapiens.org).

This indicates that LIF might provide a selective advantage in progression of different types of tumors. The tumor types where ≥10 of the patients tested have LIF mRNA levels above the error bar are: pre-B cell acute lymphatic leukemia (B-ALL), acute myeloic leukemia (AML), glioma, lung adenocarcinoma, colorectal carcinoma, bladder cancer, breast ductal cancer and breast carcinoma.

In those patients with tumors expressing high levels of LIF, LIF may act as an oncogenic factor through the regulation of cancer stem cells. Thus, blockade of LIF might be beneficial in this set of tumors, and LIF may also be used as a diagnostic and/or a prognostic factor in those patients.

The invention claimed is:
1. A method for inhibiting self-regeneration of tumor stem cells in a patient having a glioma, comprising:
 (a) quantifying the expression level of leukemia inhibitory factor (LIF) polypeptide in a glioma sample from the patient by immunohistochemistry;
 (b) comparing the expression level of LIF in said glioma sample from the patient with the expression level of LIF in a control sample, and
 (c) administering an effective amount of an anti-LIF antibody or an anti-LIF siRNA to the patient when the expression level of LIF in said glioma sample from the patient is at least 5% greater than the level in the control sample, wherein the self-regeneration of tumor stem cells is inhibited.

2. The method according to claim 1, wherein the glioma is grade IV glioma.

3. The method according to claim 1, wherein the anti-LIF antibody is a monoclonal antibody.

4. The method according to claim 1, wherein the anti-LIF antibody is a chimeric antibody.

5. The method according to claim 1, wherein the anti-LIF antibody is a humanized antibody.

6. The method according to claim 1, wherein the anti-LIF antibody is a neutralizing antibody which is detectably labelled.

7. The method according to claim 1, wherein the anti-LIF siRNA comprises bonds between nucleotides different from those found naturally.

8. The method according to claim 1, wherein the anti-LIF siRNA is detectably labelled.

9. The method according to claim 1, wherein the anti-LIF siRNA comprises modified sugars or nucleobases.

10. The method according to claim 1, wherein the anti-LIF siRNA is modified at the 3' end.

* * * * *